(12) United States Patent
Ehrhardt et al.

(10) Patent No.: US 6,943,012 B2
(45) Date of Patent: Sep. 13, 2005

(54) HELPER DEPENDENT ADENOVIRAL VECTOR SYSTEM AND METHODS FOR USING THE SAME

(75) Inventors: Anja Ehrhardt, Menlo Park, CA (US); Mark A. Kay, Los Altos, CA (US)

(73) Assignee: The Board of Trustees of the Leland Stanford Junor University, Palo Alto, CA (US)

( * ) Notice: Subject to any disclaimer, the term of this patent is extended or adjusted under 35 U.S.C. 154(b) by 423 days.

(21) Appl. No.: 10/106,831

(22) Filed: Mar. 25, 2002

(65) Prior Publication Data

US 2003/0022378 A1 Jan. 30, 2003

Related U.S. Application Data

(60) Provisional application No. 60/284,335, filed on Apr. 16, 2001, and provisional application No. 60/278,972, filed on Mar. 26, 2001.

(51) Int. Cl.[7] ............................. C12N 7/00; C12N 1/00; C12N 15/861; C12N 21/06; A01N 63/00; C07H 21/04
(52) U.S. Cl. ................. 435/320.1; 435/235.1; 435/455; 435/456; 435/457; 435/472; 435/473; 424/93.1; 424/93.2; 424/93.21; 536/23.1; 536/23.72; 536/24.1; 536/24.2
(58) Field of Search ................. 435/235.1, 455, 435/456, 457, 472, 473, 320.1; 424/93.1, 93.2, 93.21; 536/23.1, 23.72, 24.1, 24.2

(56) References Cited

U.S. PATENT DOCUMENTS

| 5,817,492 A |   | 10/1998 | Saito et al. |
|---|---|---|---|
| 5,919,676 A |   | 7/1999 | Graham et al. |
| 5,985,846 A |   | 11/1999 | Kockanek et al. |
| 6,033,885 A | * | 3/2000 | Latta et al. ................ 424/93.2 |
| 6,066,478 A |   | 5/2000 | Lusky et al. |
| 6,080,569 A |   | 6/2000 | Graham et al. |
| 6,156,497 A |   | 12/2000 | Kaleko |
| 6,228,646 B1 | * | 5/2001 | Hardy ........................ 435/455 |
| 6,468,771 B1 | * | 10/2002 | Einerhand et al. ......... 435/91.4 |

FOREIGN PATENT DOCUMENTS

| WO | WO 97/15679 | 5/1997 |
|---|---|---|
| WO | WO 97/45550 | 12/1997 |

(Continued)

OTHER PUBLICATIONS

Link, CJ. "Adenoviral vectors go retro", Feb. 2000, Nature Biotechnology vol. 18, p. 150–151.*

Zheng, C. "Genomic integration and gene expression by a modified adenoviral vector", Feb. 2000, Nature Biotechnology vol. 18, p. 176–180.*

(Continued)

*Primary Examiner*—David Guzo
*Assistant Examiner*—Michael D. Burkhart
(74) *Attorney, Agent, or Firm*—Bret E. Field; Edward J. Baba; Bozicevic, Field & Francis LLP

(57) ABSTRACT

A helper dependent adenoviral vector system is provided. The subject helper dependent adenoviral vector system is made up of: (1) a "gutless" adenoviral vector that include cis-acting human stuffer DNA that provides for in vivo long term, high level expression of a coding sequence present on the vector; (2) an adenoviral helper vector that is characterized by having an adenoviral genome region flanked by recombinase recognition sites, where the helper vectors further include a non-mammalian endonuclease recognition site positioned outside of the adenoviral genome region; and (3) a mammalian cell that expresses the corresponding recombinase and endonuclease, as well as the adenoviral preterminal and polymerase proteins. Also provided are methods of using the subject systems to produce virions having the subject helper dependent adenoviral vectors encapsulated in an adenoviral capsid. In addition, kits for use in practicing the subject methods are provided.

45 Claims, 20 Drawing Sheets

FOREIGN PATENT DOCUMENTS

| WO | WO 97/48806 | 12/1997 |
|---|---|---|
| WO | WO98/13510 | 4/1998 |
| WO | WO 98/17783 | 4/1998 |
| WO | WO99/27101 | 6/1999 |
| WO | WO00/22106 | 4/2000 |
| WO | WO00/49166 | 8/2000 |
| WO | WO 00/49168 | 8/2000 |
| WO | WO 00/49186 | 8/2000 |
| WO | WO00/52187 | 9/2000 |
| WO | WO 01/21824 | 3/2001 |

OTHER PUBLICATIONS

Recchia, A., "Site-specific integration mediated by a hybrid adenovirus/adeno-associated virus vector", PNAS, Mar. 1999. vol. 96 p. 2615–2620.*

Kazuhiro et al., "Long-term stable correction of low-density lipoprotein receptor-deficient mice with a helper-dependent adenoviral vector expressing the very low-density lipoprotein receptor", Circulation, 2001, vol. 103, no. 9.

Balague et al. "Sustained high-level expression of full-length human factor VIII and restoration of clotting activity in hemophilic mice using a minimal adenovirus vector" *Blood*, Feb. 1, 2000, vol. 95, No. 3 pp. 820–828.

Hartigan-O'Connor "Improved production of gutted Adenovirus in cells expressing Adenovirus preterminal protein and DNA Polymerase" *Journal of Virology*, Sep. 1999, vol. 73, No. 9 p. 7835–7841.

Lieber et al. "Recombinant Adenovirus with large deletions generated by cre-mediated excision exhibit different biological properties compared with first-generation vectors in vitro and in vivo", *Journal of Virology* Dec. 1996, vol. 70, No. 12, p. 8944–8960.

Morral et al. "Administration of helper-dependent adenoviral vectors and sequential delivery of different vector serotype for long-term liver-directed gene transfer in baboons" *PNAS*, Oct. 26, 1999, vol. 96. No. 22 pp. 12816–12821.

Parks et al. "Effects of stuffer DNA on transgene expression from helper-dependent adenovirus vectors" *Journal of Virology*.

Sandig et al. "Optimization of the helper-dependent adenovirus system for production and potency in vivo" *PNAS*, Feb. 1, 2000, vol. 97, No. 3, pp 1002–1007.

Schiedner et al., "Genomic DNA transfer with a high-capacity adenovirus vector results in improved in vivo gene expression and decreased toxicity" *Nature Genetics*, vol. 18, Feb. 1998 pp. 180–183.

Zheng et al. "Genomic integration and gene expression by a modified adnoviral vector" *Nature Biotechnology*, vol. 18, Feb. 2000 pp. 176–180.

Robbins et al. "Viral vectors for gene therapy" *Tibtech*, Jan. 1998, vol. 16, pp. 35–40.

Kay et al. "Viral vectors for gene therapy: the art of turning infectious agents into vehicles of therapeutics" *Nature Medicine*, vol. 7, No. 1.Jan. 2001, pp. 33–40.

Parks et al. "A helper-dependent adenovirus vector system: Removal of helper virus by Cre-mediated excision of the viral packaging signal" *Proc. Natl. Acad. Sci. USA*, vol. 93, pp. 13565–13570, Nov. 1996.

Chen et al. "Persistence in Muscle of an Adenoviral Vector that Lacks all Viral Genes" *Proc. Natl. Acad. Sci USA*, vol. 94, pp. 1645–1650, Mar. 1997.

* cited by examiner

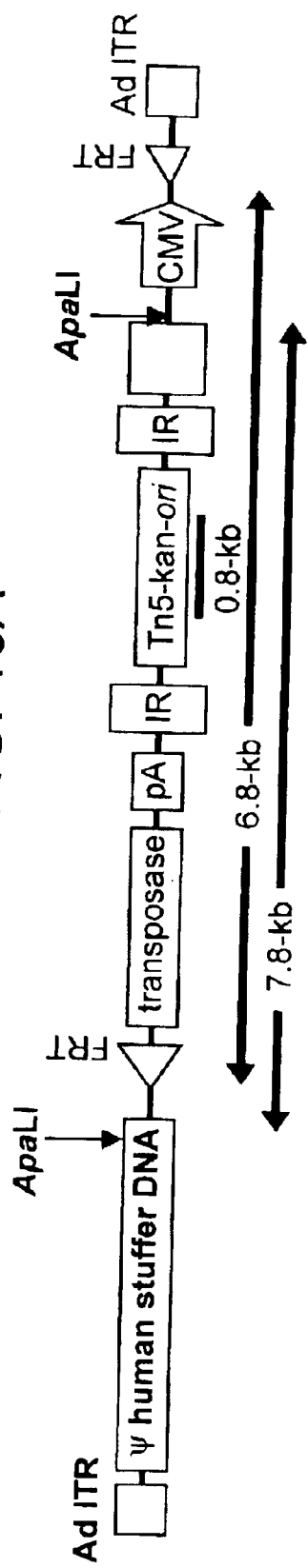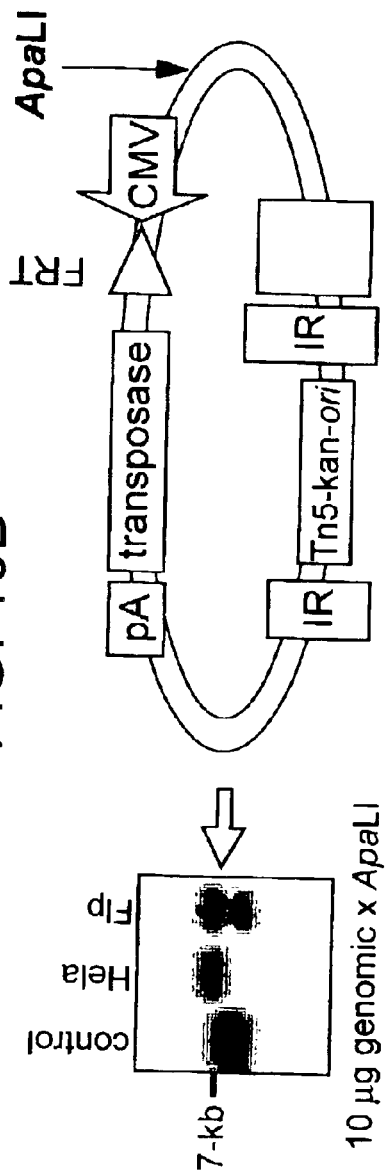
FIG. 10A
FIG. 10B

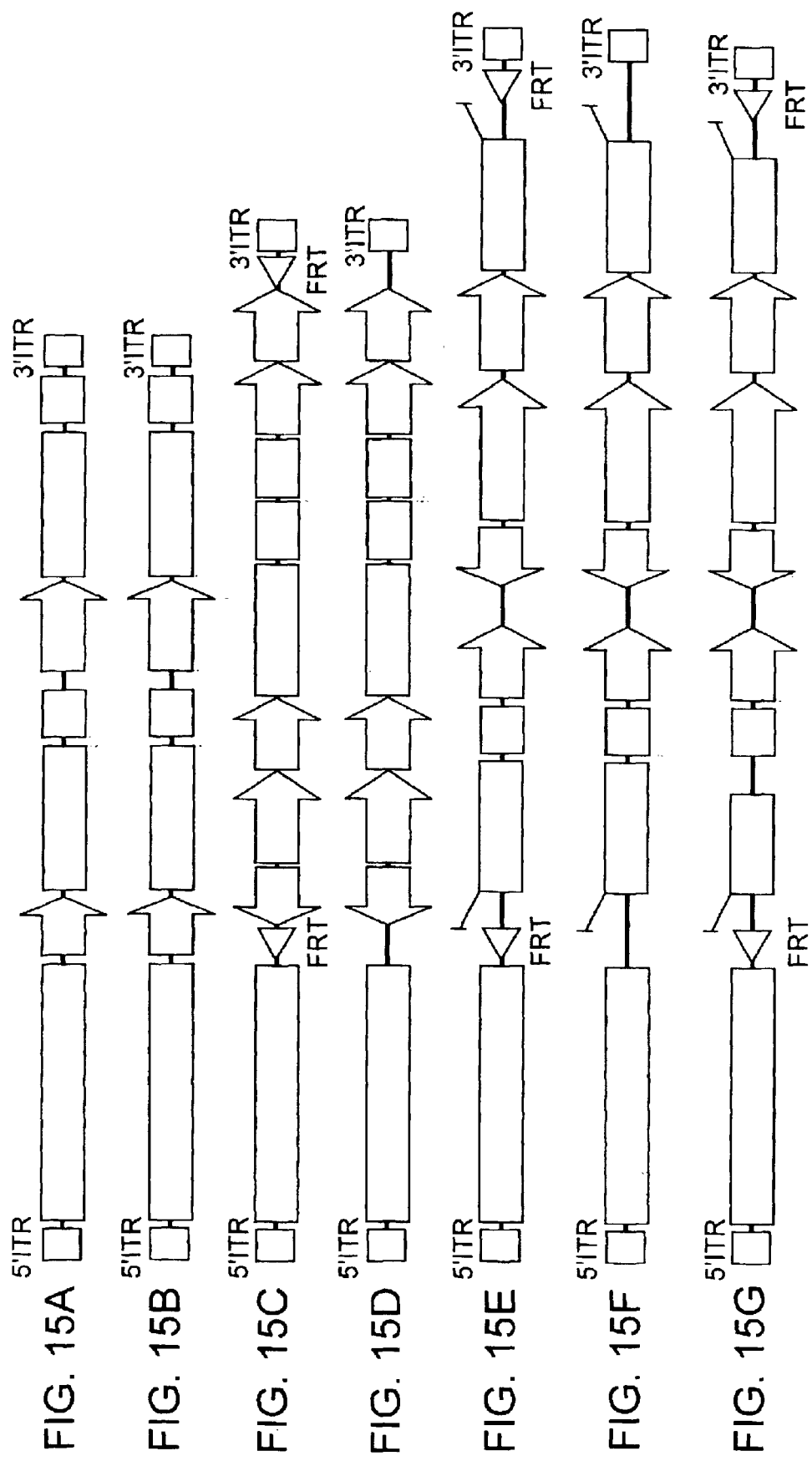

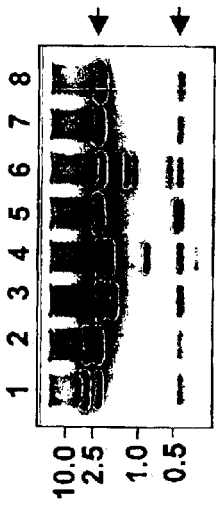

FIG. 16C

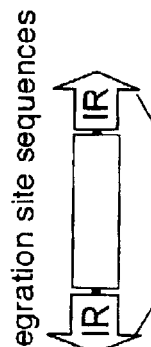

FIG. 16B

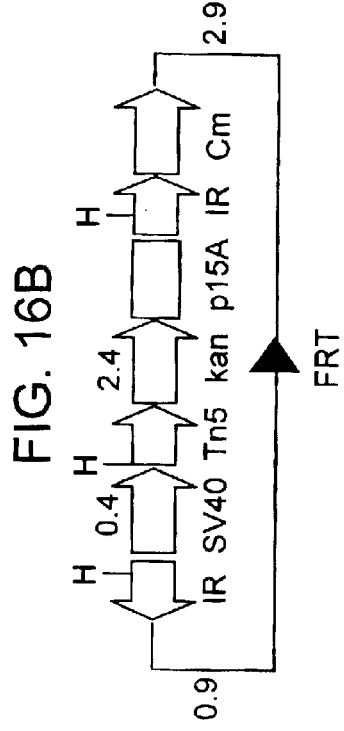

FIG. 16D

| clone | Integration site sequences | Origin | Identity | |
|---|---|---|---|---|
| 1 | aggaaataggacattTA ... TAggtgaggcaggaaca | Chrm 1 or X | | SEQ ID NO: 01 & 02 |
| 2 | gtttcagagcatgtgTA ... TAgctcttgcagaggac | Chrm 1 | mSp100-rs1(intron2) | SEQ ID NO: 03 & 04 |
| 3 | actacattgtggaaaTA ... TAtaccacattttctgt | Chrm ?? | | SEQ ID NO: 05 & 06 |
| 4 | ttagtgggaagtataTA ... TAtgcccatgtgaaagc | Chrm ?? | L1 MM repeat | SEQ ID NO: 07 & 08 |
| 5 | caaagagaaagcaggTA ... TAgcttgcagtgggctt | Ad vector | Lx2 repeat | SEQ ID NO: 09 & 10 |
| 6 | agaacacatcc-acgTA ... TAtaggcaatagctgtt | Chrm 2 | Tn5 promoter | SEQ ID NO: 11 & 12 |
| 7 | tgagtcaatcagaccTA ... TAaaatccaaggtcagcc | Chrm ?? | | SEQ ID NO: 13 & 14 |
| 8 | aagttcatttcaaaaTA ... TAgtacttgatcaccctt | Chrm 3 | MT2B repeat | SEQ ID NO: 15 & 16 |

FIG. 18B

Integration site sequences

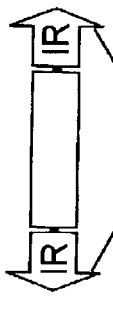

| clone | | Origin | Identity | |
|---|---|---|---|---|
| 1 | agagagacaaagaagTA tatgatatgaaaacctg | Chrm X | ORR1A-int repeat | SEQ ID NO: 17 & 18 |
| 2 | aaacacaaaagctaaTA aaatatgttttcaaaa | Chrm 6 | IG kappa CV (intron 1) | SEQ ID NO: 19 & 20 |
| 3 | ctactgtctagctttTA tatgaagctattcc | Ad vector | central alphoid repeats | SEQ ID NO: 21 & 22 |
| 4 | tttttcactgcattcTA gttgtggtttgtcca | Ad vector | transposase gene | SEQ ID NO: 23 & 24 |
| 5 | tagagtttctaaataTA taactaagaaattaa | Chrm 15 | | SEQ ID NO: 25 & 26 |
| 6 | acccagcttgtgagtTA catcagttgacaccc | Chrm 5 or 13 | | SEQ ID NO: 27 & 28 |
| 7 | ggctgagatcaaaggTA gatcacgccaggtag | Chrm 6 | | SEQ ID NO: 29 & 30 |
| 8 | tgagtcaatcagaccTA aaatccaaggtcagcc | Ad vector | Left ITR & alphoid repeats | SEQ ID NO: 31 & 32 |
| 9 | tgaggtcttaggattTA caaggaaagatatga | Chrm ?? | RLTR1-int repeat | SEQ ID NO: 33 & 34 |
| 10 | acttattgtacattaTA atatcaattaattca | Chrm ?? | LX2B repeat | SEQ ID NO: 35 & 36 |

HELPER DEPENDENT ADENOVIRAL VECTOR SYSTEM AND METHODS FOR USING THE SAME

CROSS-REFERENCE TO RELATED APPLICATIONS

Pursuant to 35 U.S.C. § 119 (e), this application claims priority to the filing date of U.S. Provisional Patent Application Ser. No. 60/278,972 filed Mar. 26, 2001 and U.S. Provisional Patent Application Ser. No. 60/284,335 filed Apr. 16, 2001; the disclosures of which are herein incorporated by reference.

ACKNOWLEDGMENT

This invention was made with United States Government support under Grant No. NIH DK 49022 awarded by National Institutes of Health. The United States Government has certain rights in this invention.

INTRODUCTION

1. Field of the Invention

The field of this invention is vectors, particularly viral vectors and more particularly adenoviral vectors.

2. Background of the Invention

Adenoviral vectors lacking all viral genes are a promising tool for safe and efficient gene transfer in vitro and in vivo (Schiedner et al., 1998, Nat Genet 18:180–3. ; Balagué et al., 2000, Blood 95: 820–828). Adenovirus has several advantages over other viral-based gene therapy approaches, including the ability to produce high titers, efficient infection of a broad range of cell types, and the ability to infect dividing and nondividing cells (Wickham et al., 1996 Nat Biotechnol 14:1570–3.). However, further development of adenoviral vectors is necessary in order to make these vectors more efficient and safer.

First generation E1-deficient adenoviruses show toxic effect of the production of immunogenic viral proteins. Therefore, the Cre-loxP HD system was developed to generate recombinant adenoviruses in which all viral coding sequences have been deleted (Parks et al., 1996, Proc Natl Acad Sci U S A. 93: 8027–8034). The helper-virus used in this system provides all adenoviral genes to the gutted adenovirus in trans. The packaging signal of these helper-viruses is flanked by loxP sites to inhibit packaging of the helper-virus genome in stable expressing Cre recombinase expressing cells. Unfortunately, even with purification the contamination level of the helper-virus remains at about 0.1% and this contamination must be further decreased in order to make gutted adenoviruses safer for gene therapy approaches.

As such, there is much interest in the development of next generation adenoviral vectors. Of particular interest would be the development of an adenoviral vector that enjoyed all of the benefits of the gutless adenoviral vectors currently available which could be produced with even lower levels of helper vector contamination. Also of interest would be the development of such a vector which could integrate into the target cell genome.

Relevant Literature

U.S. Pat. Nos. of interest include: 5,919,676; 6,066,478; 6,080,569; and 6,156,497. Published PCT applications of interest include: WO 98/13510; WO 99/27101; WO 00/22106; WO 00/49166; and WO 00/52187. Additional references of interest include: Balagué et al., Blood (2000) 95: 820–828; Hartigan-O'Connor et al., J Virol. (1999); 73:7835–41. Lieber et al., J Virol. (1996)70:8944–60; Morral et al., (1999) Proc Natl Acad Sci U S A. 96:12816–21; Parks et al., (1996) Proc Natl Acad Sci U S A. 93: 8027–8034; Parks et al., J Virol. (1999)73:13565–70; Sandig et al., Proc Natl Acad Sci U S A (2000) 97:1002–7; Schiedner et al., Nat Genet (1998)18:180–3; and Zheng et al., Nature Biotechnol (2000)18: 176–180. Additional background references of interest include: Robbins et al., Tibtech (1998) 16:35–40 and Kay et al., Nat. Med. (2001) 33–40.

SUMMARY OF THE INVENTION

A helper dependent adenoviral vector system is provided. The subject helper dependent adenoviral vector system is made up of: (1) a "gutless" adenoviral vector, which in certain embodiments includes cis-acting human stuffer DNA that provides for in vivo long term, high level expression of a coding sequence present on the vector, where in certain embodiments the vector includes an integrating domain; (2) an adenoviral helper vector that is characterized by having an adenoviral genome region flanked by recombinase recognition sites, where the helper vectors further include a non-mammalian endonuclease recognition site positioned outside of the adenoviral genome region; and (3) a mammalian cell that expresses the corresponding recombinase and endonuclease, as well as the adenoviral preterminal and polymerase proteins. Also provided are methods of using the subject systems to produce virions having the subject helper dependent adenoviral vectors encapsulated in an adenoviral capsid. In addition, kits for use in practicing the subject methods are provided.

BRIEF DESCRIPTION OF THE FIGURES

FIG. 6. Transgene expression in vitro in primary mouse hepatocytes for the HD vector AdFTC/hFIX and the first generation adenovirus fgAdhFIX. (A) Expression levels of AdFTC/hFIX in primary hepatocytes at an MOI of 1 (•/○), an MOI of 10 (▲/△) and an MOI of 100 (■/□). (B) Comparison of the transgene expression levels for AdFTC/hFIX (▲/△) and fgAdhFIX (•/○).

FIGS. 10A and 10B. Demonstration of circular transposon vector production from a gene deleted adenoviral vector in HeLa cells. HeLa cells transduced with the vector and transfected with Flp recombinase were analyzed by Southern blot.

FIGS. 15A, 15B, 15C, 15D, 15E, 15F and 15G. Structure of helper-dependent transposition vectors.

FIGS. 1 6A, 16B, 16C and 16D. Transposition from a recombinant helper-dependent adenoviral vector results in the stable insertion of transposon DNA into mouse liver chromosomes in vivo.

FIGS. 18A and 18B provide an additional diagram of the integration of a vector according to the subject invention into a genome.

DESCRIPTION OF THE SPECIFIC EMBODIMENTS

Figure 1:
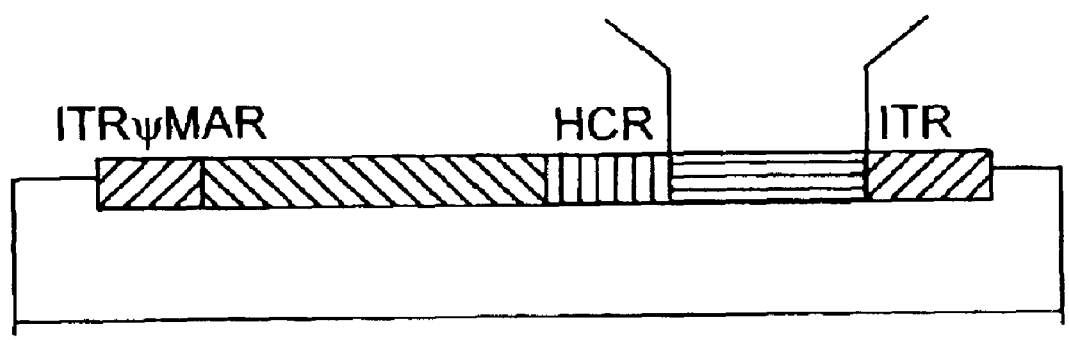
FIG. 1 provides a map of pAdFTC, which is a helper dependent vector according to the subject invention.

A helper dependent adenoviral vector system is provided. The subject helper dependent adenoviral vector system is made up of: (1) a "gutless" adenoviral vector which, in certain embodiments, includes cis-acting human stuffer DNA that provides for in vivo long term, high level expression of a coding sequence present on the vector, where in certain embodiments the vector includes an integrating nucleic acid domain; (2) an adenoviral helper vector that is characterized by having an adenoviral genome region flanked by recombinase recognition sites, where the helper vector further includes a non-mammalian endonuclease recognition site positioned outside of the adenoviral genome region; and (3) a mammalian cell that expresses the corresponding recombinase and endonuclease, as well as the adenoviral preterminal and polymerase proteins. Also provided are methods of using the subject systems to produce virions having the subject helper dependent adenoviral vectors encapsulated in an adenoviral capsid. In addition, kits for use in practicing the subject methods are provided.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

It must be noted that, as used in this specification and the appended claims, the singular forms "a," "an" and "the" include plural reference unless the context clearly dictates otherwise. Unless defined otherwise all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

All publications mentioned herein are incorporated herein by reference for the purpose of describing and disclosing components that are described in the publications which might be used in connection with the presently described invention.

In further describing the subject invention, the systems and components thereof are described first in greater detail, followed by a review of the methods of producing adenoviral virions using the subject systems, as well as a discussion of various applications in which the subject systems and methods find use and a brief description of the subject kits that can be employed to practice the subject methods.

Systems

As summarized above, the subject invention provides a system for use in producing an adenoviral vector. More specifically, the system is a system for producing an adenoviral vector particle or virion, which virion includes a nucleic acid having a sequence of interest, e.g., an expression cassette encoding a therapeutic product, in its genomic nucleic acid (nucleoid) present inside the capsid of the virion. The subject systems include, in the broadest sense, the following components: (a) a helper dependent or "gutless" adenoviral vector; (b) an adenoviral helper vector; and (c) a packaging cell line. Each of these specific elements is now discussed separately in greater detail.

Gutless Helper Dependent Adenoviral Vector

The helper dependent adenoviral vector of the subject systems is a "gutless" vector in that it is devoid of all adenoviral genes, and includes only the adenoviral ITR regions and packaging (ψ) sequence. As such, the helper dependent adenoviral vectors include no nucleic acid sequences that encode for adenoviral genome encoded products. As such, the subject gutless helper dependent adenoviral vectors do not include the adenoviral E1A, E1B pIX, IVa2, MLP, L1, L2, L3, L4, L5, E3, E2A, E2B, or E4 genes.

The helper dependent adenoviral vectors of the subject systems include at least one restriction endonuclease site. In other words, the vectors include at least one restriction site, where this site serves as a site for insertion of an exogenous nucleic acid, e.g., a nucleic acid encoding a desired therapeutic protein product. A variety of restriction sites are known in the art and may be included in this vector, where such sites include those recognized by the following restriction enzymes: HindIII, PstI, SalI, AccI, HincII, XbaI, BamHI, SmaI, XmaI, KpnI, SacI, EcoRI, and the like. In many embodiments, the vector includes a polylinker, i.e., a closely arranged series or array of sites recognized by a plurality of different restriction enzymes, such as those listed above.

In addition to the at least one restriction site, the subject helper dependent adenoviral vectors further include a stuffer region made up of a nucleic acid, particularly DNA. In certain embodiments, the domain is a region having one or more cis-acting sequences found in human genomic nucleic acids, where these one or more cis-acting sequences provide for high level and long-term in vivo expression of a coding sequence present on the vector, i.e., a coding sequence for a therapeutic protein which is present in an expression cassette of the helper dependent vector. By high level expression is meant that the expression level of the gene present on the subject helper dependent vectors is at least about 5 fold, usually at least about 10 fold and more usually at least about 25 fold higher than the expression level observed in a control helper dependent vector that does not include the subject human stuffer DNA but instead includes the ~22-kb lambda DNA fragment described in Parks et al., J. Virol. (1999) 73:8027–8034, as the stuffer DNA. The long term expression provided by the subject cis-acting human stuffer DNA is at least about 5 fold, usually at least about 10 fold and more usually at least about 25 fold longer than that which is observed in the above described control helper dependent vector. The total size of the human stuffer DNA may vary, but typically ranges from about 20 to 30 kb, usually from about 20 to 25 kb, where often the size will range from about 21 to 23 kb, e.g., 22 kb. The number of distinct cis-acting sequences which provide for the above described high level and long term expression may vary, so long as the desired expression profile is obtained, but typically ranges from about 1 to 6, usually from about 1 to 5 and more usually from about 1 to 4, wherein in many embodiments, the number of different or distinct cis-acting sequences is 2, 3 or 4. Specific cis-acting sequences of interest include, but are not limited to: a human alphaloid repeat domain, e.g., the 16.2 fragment of alphaloid repeat DNA from human chromosome 17 (as described in: Smith J G et al. Mol Cell Biol (1995) 15:5165–72); a matrix attachment region or MAR, e.g., the 4.2 kb fragment containing the left terminus of adenovirus type 5 (nt-1–440), and 2 copies of the immunoglobulin κ MAR (Igκ MAR) (as described in: Betz A G et al., Cell (1994) 77:239–248); a hepatocyte control region (HCR), e.g., the 1.2 kb fragment comprising the HCR (as described in: Miao et al., Molecular Therapy, 1:522–32); other matrix attachment regions e.g., the 2.8 kb chicken lysozyme 5' matrix attachment region (as described in Phi-Van L et al., Mol. Cell.Biol (1990) 10: 2302 2307), the MAR fragment from the 5' region of the human interferon β-gene (as described in Bode J et al. Science 1992 Jan. 10: 195–7), or other potential non-coding human sequences like e.g., other centromeric sequences or telomeric sequences; and the like. In certain embodiments, the human stuffer DNA is not the stuffer DNA disclosed in Parks et al., J. Virol. (1999) 73: 8027–8034; or the stuffer DNA found in pSTK120 or other stuffer DNA disclosed in Sandig et al., Proc. Nat'l Acad. Sci. U S A (Feb. 1, 2000)97(3):1002–7.

As mentioned above, and in addition to the restriction site(s) and the stuffer DNA, the subject helper adenoviral vectors also include an adenoviral packaging sequence and flanking adenoviral ITRs, where the nucleic acid sequences for these elements are known and nucleic acids comprising these elements are readily available to those of skill in the art. By flanking is meant that there is a single ITR sequence at either end of the helper dependent vector, or at least region of the vector that includes the above described packaging sequence, restriction site and human stuffer fragment.

In addition, the subject helper dependent adenoviral vectors typically further include an expression cassette that includes a nucleic acid encoding a product of interest operably linked to a promoter (as well as any other required sequences to provide for a functional expression cassette), which is also referred to herein as a "gene of interest." Specific products of interest and their corresponding encoding sequences are described in greater detail infra. The size of the expression cassette may vary, but generally ranges from about 1 kb to 14 kb, usually from about 4 kb to 11 kb and more usually from about 5 kb to 9 kb.

In certain embodiments, the expression cassette of the subject helper dependent vectors is part of an integrating element. By integrating element is meant a section, region or piece of DNA that, in the presence of a DNA integration mediating enzyme or activity, integrates into chromosomal DNA. The integrating element may be a random or site specific integrating element. Random integrating elements are elements that, in the presence of an appropriate DNA integration mediating enzyme or activity, integrate into chromosomal DNA at random locations. Examples of randomly integrating elements are transposons, which include the expression cassette flanked by sequences recognized by a transposase. The integrating element may be any convenient transposon, where a number of transposon systems (i.e., transposases and the sequences recognized thereby) are known in the art and include: the Sleeping Beauty transposon, the P-element transposon, and other transposable elements of the Tc1/mariner superfamily, and the like. Alternatively, the integrating element may be a site-specific integrating element. Site-specific integrating elements of interest include integrase recognized elements. A number of integrases are known in the art, where representative integrases include, but are not limited to: the Φc31 integrase described in Groth et al. Proc. Nat'l Acad. Sci USA (2000) 97:5995–6000; the Cre recombinase described in Sauer et al. Curr. Opin. Biotechnol. (1994) 5, 521–527 3) and the FLP recombinase as described in Diaz, V. et al. J. Biol. Chem. (1999) 274, 6634–6640; and the like. See also WO 00/11155 and WO 01/61049; the disclosures of the priority documents of which are herein incorporated by reference.

In certain preferred embodiments, the integrating element is flanked by recombinase recognition sites that are capable of recombining with each other in the presence of the appropriate recombinase to produce a circular integrating element from the initial linear helper dependent nucleic acid material. Recombinase recognition sites of interest include, but are not limited to: lox sites, att sites, dif sites and frt sites, where sites of interest include, but are not limited to: loxP, loxP2, loxP511, loxP514, loxB, loxC2, loxL, loxR, loxΔ86, loxΔ117, loxP3, loxP23, att, dif and frt, and the like.

The specific recombinase sites chosen to be present in the expression cassette and flank the expression cassette, e.g., in those embodiments where a circular integrating element is desired, are selected based on the recombinase of the helper vector genome and the nature of the target cell, as well any additional vectors that will be administered with the helper dependent vector. Generally, the recombination recognition sites present on the helper dependent vector are different from those present on the helper vector. In addition, the flanking sites are different from the site presentin the expression cassette.

In those embodiments where the helper dependent vector includes an integrating element, e.g., an element including a first recombinase recognition site and flanked by second recombinase recognition sites that recombine with each other, the helper dependent vector may further including coding sequences for one of, or even both of, the recombination recognition sites present on helper dependent vector. For example, when the helper dependendent vector includes an integrating expression cassette that includes sleeping beauty recombinase recognition site, where the expression cassette is flanked by FRT sites, the helper dependent vector may further included coding sequences for the sleeping beauty transposase and/or Flp recombinase. When present, these coding sequences are typically present as part of an expression cassette so that they are expressed in the target cell. Furthermore, the coding sequences are typically located on a region of the helper dependent vector that is not flanked by the recombinase recognition sites, e.g., they may be located in the stuffer DNA domain, as described above, so that the coding sequences do not become part of an excised circular element that is ultimately integrated into the target cell genome.

The overall size of the helper dependent vector will vary, but generally ranges from about 22 to 38, usually from about 25 to 36 and more usually from about 26 to 33 kb. The helper dependent vector may be linear or circular, e.g., a plasmid, depending on the particular system and protocol in which the vector is to be used. In certain embodiment, the helper dependent vector may be encapsulated in an adenoviral capsid.

Figure 8:
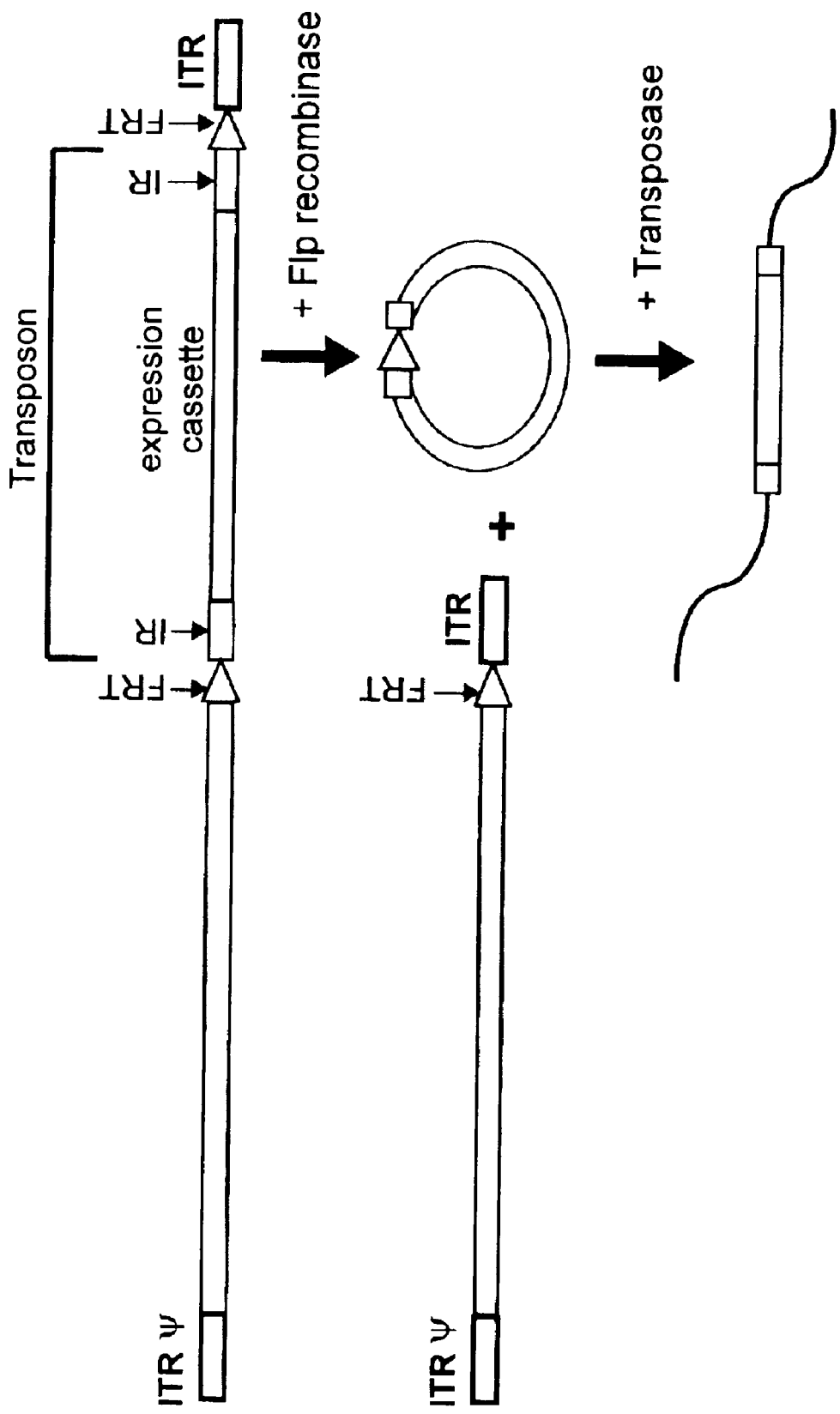
FIG. 8 provides a map of a helper dependent vector according to the subject invention that includes an expression cassette in an excisable transposon.

A depiction of a representative helper dependent vector according to the subject invention is provided in FIG. 1. A depiction of a helper dependent vector in which the expression cassette is present as a transposon that can be cut out of the vector to produce a circular nucleic acid in the presence of a recombinase, i.e., an expression cassette present in an excisable transposon, is shown in FIG. 8.

Adenoviral Helper Vector

Another element of the subject systems is the helper vector, which vector is an adenoviral helper vector. The adenoviral helper vector includes an adenoviral vector coding sequence that provides at least a portion of the adenoviral genome encoded products necessary for replication and packaging of the gutless helper dependent adenoviral vector, described above, where these products are provided in trans to the helper dependent vector. Typically, the adenoviral vector coding sequence of the helper vector supplies the following adenoviral genome encoded products in trans: gene products of the E2A, E2B, E4 region and the gene products of the late adenoviral coding regions L1, L2, L3, L4 and L5, where the particular factors provided in trans by the helper vector may depend, at least in part, on the nature of the packaging cell that is employed, which may or may not provide for a portion of the requisite adenoviral genome encoded factors in trans. As such, the helper vectors of the subject systems include an adenoviral vector coding sequence that includes all of or portion of the wild type adenoviral vector coding sequence. Typically, the portion of the adenoviral vector coding sequence present in the helper vector ranges from about 70 to 99, usually from about 80 to 95 length % of the total adenoviral genome. The length of this adenoviral vector coding element typically ranges from about 20 kb to 38 kb, usually from about 25 kb to 32 kb and more usually from about 26 kb to 28 kb.

The above described adenoviral vector coding element is positioned in a first region of the helper vector between first and second recombinase recognition sites that recombine with each other and are recognized by the same recombinase. Recombinase recognition sites of interest include, but are not limited to: lox sites, att sites, dif sites and frt sites, where specific sequences of interest include, but are not limited to: loxP, loxP2, loxP511, loxP514, loxB, loxC2, loxL, loxR, loxΔ86, loxΔ117, loxP3, loxP23, att, dif, and frt, and the like. Where the gutless helper dependent vector of the system in which the subject helper vector is employed includes an excisable integrating element on which the expression cassette is found, as described above, the recombinase recognition sites of the helper vector are not recognized by the same recombinase as those sites of the helper dependent vector.

In addition to the above described recombinase recognition site flanked adenoviral vector coding element, the helper viral vector of the subject systems further includes at least one endonuclease recognition site not found in mammalian genomic sequences (i.e., a non-mammalian restriction site), where this non-mammalian restriction site is located in a region of the helper dependent vector that is other than the region flanked by the recombinase recognition sites which includes the adenoviral vector coding element. Thus, where the helper vector is a linear vector, this non-mammalian restriction site is located on the vector to the left of the 5' recombinase recognition site or to the right of the 3' recombinase recognition site. In other embodiments where the helper vector is circular, e.g., a plasmid, when viewed as having two regions separated by the recombinase recognition sites, the adenoviral coding sequence element and the non-mammalian restriction site are positioned on different regions of the circular vector. The size of the non-mammalian restriction site may vary, but typically is at least about 6 nt long, usually at least about 12 nt long and more usually at least about 16 nt long, where the length of the site may be as long as 38 nt or longer, but in certain embodiments does not exceed about 30 nt and typically does not exceed about 20 nt nt. Any convenient non-mammalian restriction site may be employed, where representative sites of interest include, but are not limited to: the 26 nt I-CeuI, the 39 nt PI-SceI and the 18 bp I-Sce I site, and the like, where in many embodiments of interest the site is the 18 bp I-Sce I site. The presence of the non-mammalian restriction site makes the helper vector self-destroying when the vector is present in a host cell that expresses the corresponding restriction endonuclease, i.e., the nuclease that cuts the site.

In addition to the adenoviral vector coding element, flanking recombinase recognition sites and non-mammalian restriction site described above, the helper vectors of the subject systems also typically include a packing sequence and end flanking ITR sequences, as described above.

The helper virus typically ranges in length from about 30 kb to 38 kb, usually from about 34 kb to 38 kb and more usually from about 36 kb to 38 kb. The helper virus vector may be linear or circular, and may be encapsulated in a capsid, e.g., an adenoviral capsid, such that the helper virus vector is a virion.

Figure 3:
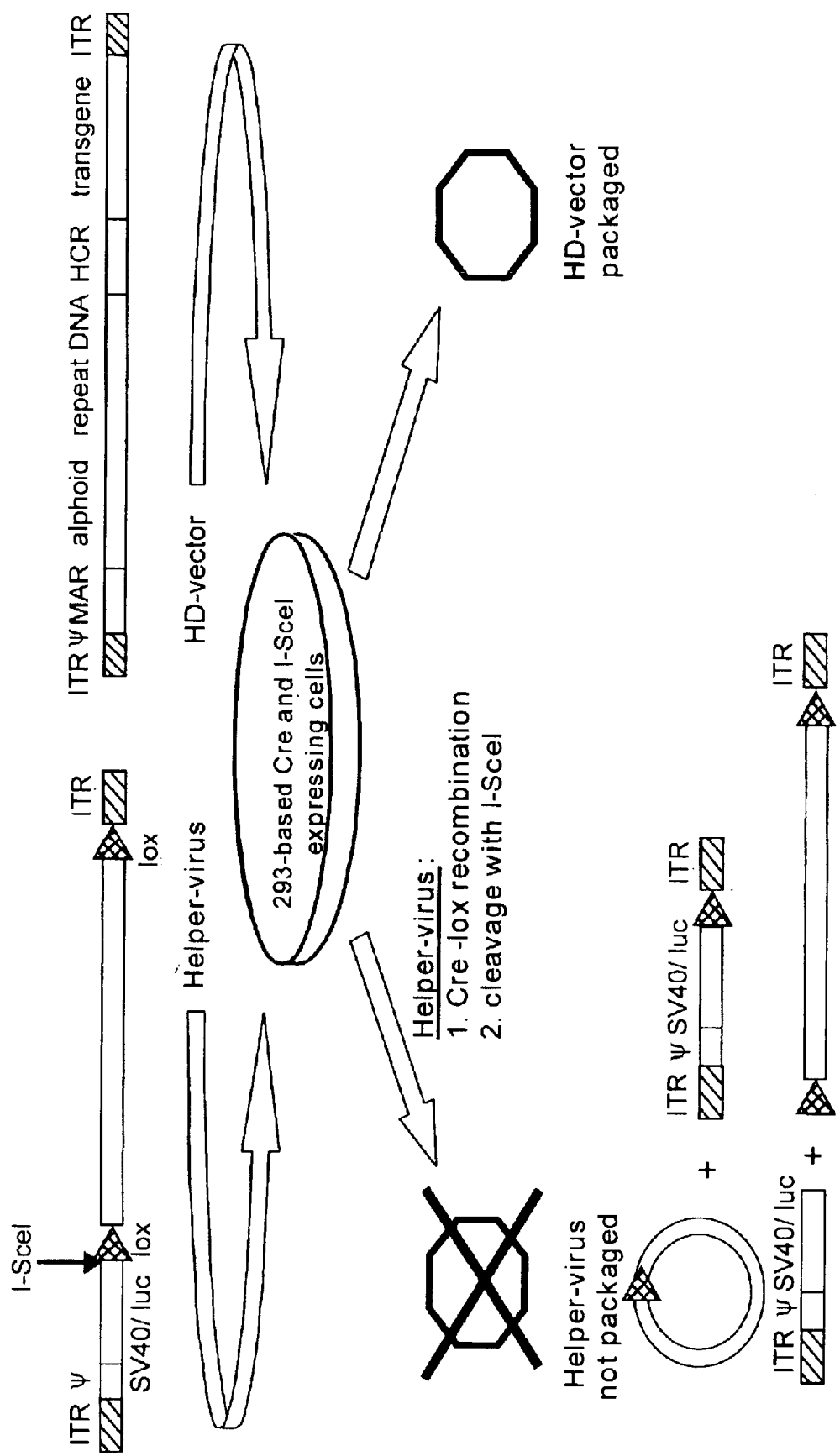
FIG. 3 provides a map of a schematic of the vector production system according to the subject invention.

A map of a representative helper virus is provided in FIG. 3.

Packaging Cell

The third component of the subject systems is the packaging cell. The packaging cell of the subject invention is a mammalian cell that stably expresses: (i) the recombinase that recognizes the recombinase recognition sites of the helper vector; and (ii) the endonuclease that recognizes, i.e., cleaves, the non-mammalian restriction site of the helper vector. In certain preferred embodiments, this packaging or host cell also expresses the adenoviral preterminal protein, and the adenoviral polymerase. Generally, the mammalian cell is a human cell, where in certain preferred embodiments the cell is an immortalized cell. Representative cells of interest include, but are not limited to: adenovirus type 5 DNA immortalized human embryo kidney cells, e.g., HEK cells such as HEK293 cells, and the like.

The recombinase that is stably expressed by the subject packaging cells may vary. Representative recombinases of interest include, but are not limited to: Cre recombinase (the cre gene has been cloned and expressed in a variety of hosts, and the enzyme can be purified to homogeneity using standard techniques known in the art—purified Cre protein is available commercially from Novagen); FLP recombinase of *S. cerevisiae* that recognizes the frt site; Int recombinase of bacteriophage Lambda that recognizes the att site; xerC and xerD recombinases of *E.coli*, which together form a recombinase that recognizes the dif site; the Hin recombinase; the Cin recombinase; the immunoglobulin recombinases; and the like. Because the cell stably expresses the desired recombinase, it is typically a cell that has been engineered to stably express the recombinase, e.g., through transformation with a transgene that includes an expression cassette or requisite portion thereof for the transgene.

In addition to the recombinase, the mammalian cell also stably expresses the non-mammalian restriction endonuclease that recognizes and cuts the non-mammalian restriction site of the helper vector, as described above. This non-mammalian restriction endonuclease may vary, where representative endonucleases include, but are not limited to: I-CeuI, PI-SceI, I-SceI, and the like, where in many embodiments the packaging cell stably expresses I-SceI. As with the recombinase, the cell is generally engineered to express the restriction endonuclease, e.g., via transformation with a transgene that includes an expression cassette for the restriction endonuclease or requisite portion thereof.

In certain embodiments, the packaging cell is further characterized in that it stably expresses the adenoviral preterminal protein and the adenoviral polymerase, e.g., the cell has been transformed to stably express these adenoviral factors. A specific packaging cell of interest is the 293 based cell, 294G, described in greater detail in the experimental section infra, as well as the other specific packaging cells described in the experimental section, infra.

Also provided are collections or populations of the above-described packaging cells, e.g., a cell line.

Methods of Producing Packaged Gutless Adenoviral Vectors

Also provided are methods of using the subject systems to produce packaged helper dependent gutless adenoviral vectors, i.e., virions that include the gutless helper dependent adenoviral vectors described above.

In general, the subject methods require contacting a packaging cell, typically a collection or cell line of packaging cells (e.g., a population of at least about $1 \times 10^6$, usually at least about $1 \times 10^6$ cells), of the subject systems as described above with the helper vector and helper dependent vector of the subject systems under conditions that result in entry of the helper dependent adenoviral vector and the adenoviral helper vector into the packaging cell. Contact may occur in any convenient manner so long as entry of the requisite vectors occurs, where contact may be simultaneous or sequential. A representative contact protocol is described in the experimental section, infra. The above contacting step is also known as transfecting. Transfection is carried out using any convenient protocol, where suitable protocols are known to those of skill in the art and a representative protocol is provided in the experimental section infra.

Following contact and vector entry, the resultant cells are maintained under conditions sufficient to produce virions or viral particles that are made up of the helper dependent adenoviral vector encapsulated in an adenoviral capsid. Typically, the cells are maintained at a temperature ranging from about 35 to 39°, usually from about 36.5 to 37.5° C. for a period of time ranging from about 1 day to 7 days, usually from about 1 day to 4 days on a suitable growth medium, e.g., Dulbecco's Modified Eagle Medium and the like.

As such, following transfection, the transfected host cells are grown and recombinant adenovirus according to the subject invention is harvested therefrom, where any convenient protocol including standard protocols known to those of skill in the art may be employed for these steps. See e.g., the experimental section, infra.

FIG. 3 provides a schematic representation of the subject methods of producing packaged helper dependent adenoviral vectors. As shown in FIG. 3, when present in the packaging cell expressing the relevant recombinase protein, the adenoviral vector encoding element of the helper vector that is flanked by the recombinase recognition sites is excised from the remainder of the helper vector, which remainder is then cut by the non-mammalian restriction enzyme. Nonetheless, the requisite adenoviral encoded factors are still provided in trans by the excised recombinase site flanked adenoviral vector coding element. The helper dependent vector is therefore packaged into viral particles with the trans provided factors and factors provided by the host packaging cell, e.g., the adenoviral polymerase and preterminal protein.

The above method produces high titre preparations of packaged helper dependent vector with extremely low amounts of helper vector contamination. By high titre preparation is meant a preparation with at least about $5 \times 10^9$, usually at least about $1 \times 10^{10}$ and more usually at least about $5 \times 10^{10}$ particles/ml. The amount of helper virus contamination in the subject high titre preparations does not exceed about 1%, usually does not exceed about 0.2% and more usually does not exceed about 0.1%, where in certain embodiments the amount of helper virus contamination is much lowere, e.g., 0.05%, 0.02% or lower.

Intergating Adenoviral Vectors

In addition to the above-described helper dependent vectors that include an integrating expression cassette, the subject invention also provides adenoviral vectors in general that include an integrating element. In the broadest sense, any adenoviral vector can be modified to including an integrating element as described herein, where the integrating element typically includes an expression cassette including a first recombinase recognition site, where the expression cassette is flanked by second recombinase recognition sites that recombine with each other. Representative adenoviral vectors that may be modified to be integrating vectors according to the present invention include those described in U.S. Pat. Nos. 5,962,313; 5,962,311; 5,952,221; 5,932,210; 5,928,944; 5,922,576; 5,919,676; 5,891,690; 5,885,808; 5,880,102; 5,877,011; 5,871,982; 5,869,037; 5,858,351; 5,851,806; 5,843,742; 5,837,484; 5,820,868; 5,789,390; 5,756,283; 5,747,072; 5,731,172; 5,700,470; 5,670,488; 5,616,326; 5,589,377; 5,585,362; 5,354,678; the disclosures of which are herein incorporated by reference.

Utility

The helper dependent adenoviruses produced with the subject systems using the protocol described above, and/or the adoviral vectors that include an integrating element, e.g., integrating expression cassette, can be used as vectors to stably insert a wide variety of endogenous and/or exogenous nucleic acids into a target cell (exogenous means a nucleic acid having a sequence that is not present in the target cell while endogenous means a nucleic acid that pre-exists in the target cell, prior to insertion, e.g., where one wishes to insert extra copies of the nucleic acid and/or expressable copies of the nucleic acid into the target cell). In many embodiments, the sequence of nucleotides present in the exogenous nucleic acid will be one that is not found in the genome of the target cell, i.e., it will be heterologous to the target cell. The subject methods can be used with a variety of target cells. Target cells with which the subject vectors may be employed are generally animal cells. Of particular interest in many embodiments is the use of the subject vectors to target vertebrate cells, particularly avian cells, e.g., chicken cells; mammalian cells, including murine, porcine, ovine, equine, rat, dog, cat, monkey, and human cells; and the like.

In the methods of the subject invention, the adenovirus vector is contacted with a target cell under conditions sufficient for the adenovirus to insert its genome, i.e., the helper dependent vector nucleic acid described above, into the target cell. Any convenient protocol may be employed, where the protocol may provide for in vitro or in vivo introduction of the genome into the target cell. For example, where the target cell is a cell of an organism that has been removed from the organism, the recombinant virus may be contacted with the cell under cell culture conditions permissive of viability of the target cell. Alternatively, where the target cell or cells are part of a multicellular organism, the adenoviral vector may be administered to the organism or host in a manner such that the virus enters the organism and inserts its genome into the target cell(s). For example, virus may be injected into the organism or host, contacted with a mucosal surface of the host and the like.

The subject methods of stable integration of exogenous nucleic acid into the genome of a target cell using the subject adenoviral vectors find use in a variety of applications in which the stable integration of an exogenous nucleic acid into a target cell is desired.

Depending on the particular nature of the adenoviral vector, the exogenous nucleic acid may or may not integrate in the target cell genome. As such, in certain embodiments, the inserted helper dependent vector is episomally present in the target cell.

In yet other embodiments, the inserted helper dependent vector, or more specifically a portion thereof, integrates into the host cell genome. As described above, in certain embodiments the exogenous nucleic acid, e.g., expression cassette, is present in an integrating element, either random or site specific, that may or may not be excisable from the vector by a recombinase. This mechanism of integration is schematically shown in FIG. 8. In FIG. 8, when the helper dependent adenoviral genome with the expression cassette is inserted into the target cell that expresses the appropriate recombinase and transposase, the integrating element is excised from the vector to produce a circular intermediate which is then transposed into the target cell genome. In this manner, integration of the exogenous nucleic acid of the vector into the target cell genome occurs.

Applications in which the subject vectors and methods find use include: research applications, polypeptide synthesis applications and therapeutic applications. Each of these representative categories of applications is described separately below in greater detail.

Research Applications

Examples of research applications in which the subject vectors find use include applications designed to characterize a particular gene. In such applications, the vector is employed to insert a gene or coding sequence of interest into a target cell and the resultant effect of the inserted gene on the cell's phenotype is observed. In this manner, information about the gene's activity and the nature of the product encoded thereby can be deduced. The vectors can also be employed to identify and define DNA sequences that control gene expression, e.g. in a temporal (e.g. certain developmental stage) or spatial (e.g. particular cell or tissue type) manner. In such assays, the subject vectors are employed to stably integrate into the genome of a target cell a selectable marker gene, e.g. antibiotic resistance, LacZ, etc., where the vector lacks a sufficient promoter for the marker gene such that the marker is not significantly expressed, if at all, unless it is underneath an endogenous promoter element. If the marker gene is inserted into the target cell genome in sufficient relationship to an endogenous promoter sequence, it will be expressed. From the resultant expression profile of the marker gene, the endogenous promoter that is mediating its expression can then be characterized. Yet another research application in which the subject vectors find use is in the identification and characterization of the results of gene expression studies. For example, a plurality of distinct vector targeted cells (or animals produced therefrom) are prepared in which the gene of interest is inserted into distinct locations in the genome of various targeted cells, where expression of the gene of interest is dependent on endogenous promoter mediation, i.e. where the gene of interest lacks a promoter or is coupled to only a weak promoter. By plurality is meant at least two, where the number usually ranges from about 2 to 5000, usually from about 2 to 200. This plurality of vector targeted cells may be produced by introducing the vector in a plurality of cells or taking a collection of pretargeted cells that are homogenous with respect to the insertion site of the gene, i.e. progeny of a single targeted cell, and then introducing transposase into one or more of, but not all of, the constituent members of the collection. The subject vectors can also be used to study integration mutants, where a gene of interest is inserted randomly into the genome and the impact of this random insertion of the targeted cell phenotype are observed. One can also employ the subject vectors to produce models in which overexpression and/or misexpression of a gene of interest is produced in a cell and the effects of this mutant expression pattern are observed. One can also use the subject vectors to readily clone genes introduced into a host cell via insertional mutagenesis that yields phenotypes and/or expression patterns of interest. In such applications, the subject vectors are employed to generate insertional mutants through random integration of DNA. The phenotype and/or expression pattern of the resultant mutant is then assayed using any convenient protocol.

Polypeptide Synthesis Applications

In addition to the above research applications, the subject vectors also find use in the synthesis of polypeptides, e.g. proteins of interest. In such applications, a vector that includes a gene encoding the polypeptide of interest in combination with requisite and/or desired expression regulatory sequences, e.g. promoters, etc., (i.e. an expression module) is introduced into the target cell that is to serve as an expression host for expression of the polypeptide. Following introduction and subsequent stable integration into the target cell genome, the targeted host cell is then maintained under conditions sufficient for expression of the integrated gene. Once the transformed host expressing the protein is prepared, the protein is then purified to produce the desired protein comprising composition. Any convenient protein purification procedures may be employed, where suitable protein purification methodologies are described in Guide to Protein Purification, (Deuthser ed.) (Academic Press, 1990). For example, a lysate may be prepared from the expression host expressing the protein, and purified using HPLC, exclusion chromatography, gel electrophoresis, affinity chromatography, and the like.

Therapeutic Applications

The subject vectors also find use in therapeutic applications, in which the vectors are employed to stably integrate a therapeutic nucleic acid, e.g. gene or protein/factor coding sequence thereof, into the genome of a target cell, i.e. gene therapy applications. The subject vectors may be used to deliver a wide variety of therapeutic nucleic acids. Specific therapeutic genes for use in the treatment of genetic defect based disease conditions include genes encoding the following products: factor VIII, factor IX, β-globin, low-density lipoprotein receptor, adenosine deaminase, purine nucleoside phosphorylase, sphingomyelinase, glucocerebrosidase, cystic fibrosis transmembrane conductance regulator, α-antitrypsin, CD-18, ornithine transcarbamylase, argininosuccinate synthetase, phenylalanine hydroxylase, branched-chain α-ketoacid dehydrogenase, fumarylacetoacetate hydrolase, glucose 6-phosphatase, α-L-fucosidase, β-glucuronidase, α-L-iduronidase, galactose 1-phosphate uridyltransferase, interleukins, cytokines, small peptides, and the like. The above list of proteins refers to mammalian proteins, and in many embodiments human proteins, where the nucleotide and amino acid sequences of the above proteins are generally known to those of skill in the art. Cancer therapeutic genes that may be delivered via the subject vectors include: genes that enhance the antitumor activity of lymphocytes, genes whose expression product enhances the immunogenicity of tumor cells, tumor suppressor genes, toxin genes, suicide genes, multiple-drug resistance genes, antisense sequences, and the like.

Uses of adenoviral vectors are further described in U.S. Pat. Nos. 5,962,313; 5,962,311; 5,952,221; 5,932,210; 5,928,944; 5,922,576; 5,919,676; 5,891,690; 5,885,808; 5,880,102; 5,877,011; 5,871,982; 5,869,037; 5,858,351; 5,851,806; 5,843,742; 5,837,484; 5,820,868; 5,789,390; 5,756,283; 5,747,072; 5,731,172; 5,700,470; 5,670,488; 5,616,326; 5,589,377; 5,585,362; 5,354,678; the disclosures of which are herein incorporated by reference.

Transgenic Cells and Non-Human Transgenic Animals

Also provided by the subject invention are transgenic cells and non-human transgenic animals. A feature of the subject cells and animals that include the same is the presence of the subject recombinant adenovirus in the cell, e.g. either on a vector in the cell or stably integrated the cell's genome. Similarly, the transgenic animals of the subject invention are characterized by include at least one transgenic cell, as described supra.

Kits

Also provided by the subject invention are kits for preparing the subject recombinant adenoviral vectors, as described above. The subject kits at least include one or more of, usually all of: a helper dependent vector, a helper vector and a packaging cell, as described above. Other optional components of the kit include: restriction enzymes, control plasmids; buffers; etc. The various components of the kit may be present in separate containers or certain compatible components may be precombined into a single container, as desired.

In addition to above-mentioned components, the subject kits typically further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

The following examples are offered by way of illustration and not by way of limitation.

EXPERIMENTAL

I. Preparation of Vectors and Packaging Cell

A. Helper Dependent Vector pAdFTC:

A new helper-dependent vector pAdFTC was developed. This vector contains three cis-acting sequences as stuffer DNA: a human fragment of alphoid repeat DNA (CEN), a Matrix Attachment Region (MAR), and the hepatocyte control region (HCR). AdFTC also contains a multiple cloning site which allows production of deleted adenoviruses with any gene of interest. A map of this vector is provided in FIG. 1.

The plasmid pAdFTC for adenoviral production is based on the plasmid pDYAL containing a 16.2 kb fragment of alphaloid repeat DNA from human chromosome 17 (Krysan and Calos, Gene. 1993 Dec. 22;136(1–2):137–43.). The alphaloid repeat DNA is flanked by a 1.5 kb fragment containing the left terminus of adenovirus type 5 and 2 copies of the IgK MAR. The subclone pDYAL5'ITRIgKMAR was obtained by cloning the SalI fragment from p72N5'ITRIgKMAR into the Sal I site of pDYAL. The 1.2 kb Spe I fragment from pHM5 3'ITRHCR containing the hepatocyte control region (HCR), a multiple cloning site with recognition sites for the restriction endonucleases PacI and PmeI and the right terminus of adenovirus type 5 was cloned into the SpeI site of pDYAL5'ITRIgKMAR resulting in pAdFTC. A shuttle plasmid pBS-P/P based on pBS K/S (STRATAGENE) was consructed with a multiple cloning site in between a Pac I and PmeI recognition site. The PacI site was cloned by PacI linker ligation into the KpnI site of pBS and PmeI was cloned by linker ligation into the SacI site of pBS resulting in pBS-P/P.

B. Packaging Cell 294G:

A new 293 based cell line, 294G, was developed for efficient gutless adenoviral production. 294G stably expresses the adenoviral genes preterminal protein and polymerase, Cre/loxP recombinase, and the restriction enzyme endonuclease I-SceI. I-SceI is an intron encoded endonucleases that recognize 18 bp nonpalindromic sequences that are so unique they are not present in mammalian cells. This feature allows for this restriction enzyme to be stably produced in mammalian cells. For production of the cell line 294G stably expressing I-SceI, the I-SceI cDNA was cloned into the plasmid pIRESpuro vector (CLONTECH) and stably transfected into 293 based cells.

C. Helper Vectors

1. Helper Vector AdlucI(lox)$_2$:

A new helper-virus AdlucI(lox)$_2$ was developed for gutless adenoviral production. This helper virus can be destroyed during gutless adenovirus production to circumvent the problem of helper-virus contamination. AdlucI (lox)$_2$ contains I-SceI recognition site(s) and therefore can be cleaved and destroyed in stably I-SceI expressing cells. In addition AdlucI(lox)$_2$ contains two loxP sites flanking the whole adenoviral genome. The adenoviral vector was constructed by cloning the luciferase gene driven by the SV40 promter was cloned into the shuttle vector pHM5lox and one or two sites in the multiple cloning site was changed to I-SceI. The I-CeuI/PI-SceI fragment containing the SV40/luciferase expression cassette was cloned into the I-CeuI/PI-SceI site of pAdHM4lox. Vectors contains lacZ or GFP as marker genes were constructed as well. First generation adenoviruses were produced and amplified as previously described (Mizuguchi and Kay, Hum Gene Ther. 1998 Nov. 20;9(17):2577–83.).

2. Generation of helper-virus Adluc/IsceI(lox)$_2$

Figure 2:
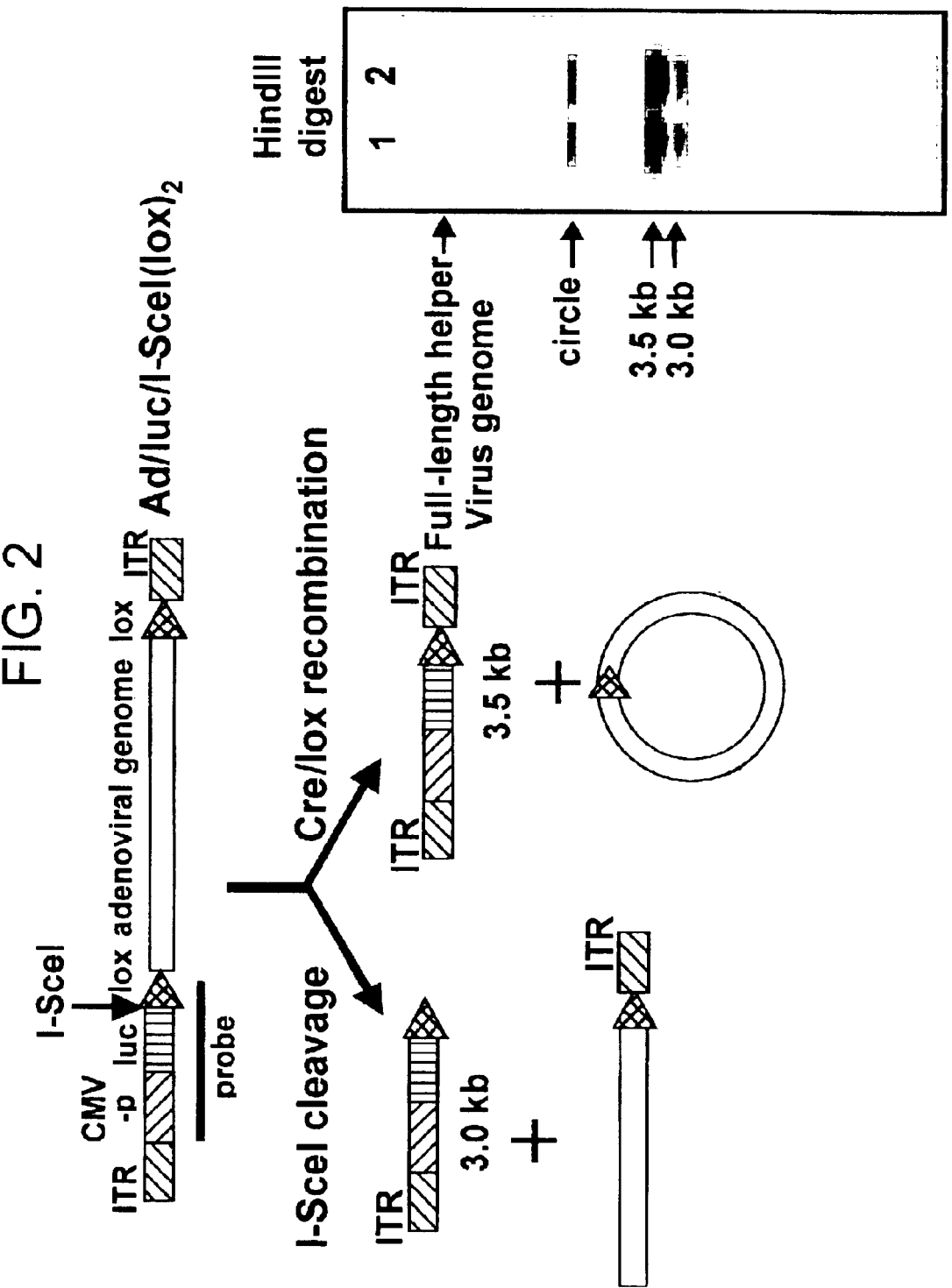
FIG. 2. Structure of the new helper virus Adluc/IsceI(loX)$_2$. The formation of the helper-virus IsceI cleavage and Cre-recombination products after infection of C7-Cre/SceI cells is demonstrated by Southern Blot.

The helper virus [Adluc/IsceI(lox)$_2$] was constructed containing an I-SceI intron encoded endonuclease restriction site (FIG. 2). Additionally, a new cell line for producing gene deleted vectors was developed. We have modified the Cre-C7 cells and selected a clone that expresses the functional endonuclease. To verify that the products predicted are actually produced after transduction of the new helper virus into the C7-Cre/SceI cell lines we have performed a preliminary Southern analysis (FIG. 2) on the Cre/SceI cells infected with the vector and helper confirming their presence. The important point is that a circular adenoviral genome that is capable of expressing adenoviral proteins in trans (to allow for replication and packaging of the vector) but is devoid of a packaging signal is produced.

II. Adenoviral Preparation Protocol:

The strategy to produce high capacity adenoviruses containing decreased amounts of helper virus contamination using the above described components is described below and demonstrated in FIG. 3. As mentioned above, the removal of helper virus from viral stocks is a limiting factor for continued clinical use of the HD vector system. The strategy of the present invention substantially reduces, if not eliminates, such helper virus contaminants. In the presence of Cre recombinase, the whole adenoviral coding sequence of the helper-virus of the present invention is deleted, which results in unstable adenoviral mini-genomes (Lieber et al., J Virol. (1996) 70:8944–60) and a circular form of the deleted adenoviral genome without packaging signal. I-Sce I recognition sites present in our new helper-virus are recognized in stable expressing I-Sce cell lines during viral production which results in cleavage of the helper-virus genome without packaging of the cleavage products. This combination of Cre/lox recombination and the cleavage of the helper-virus genome by the restriction enzyme I-Sce I during production decreases the helper-virus contamination significantly.

To produce HD-vectors with the new helper-virus, a 293 based cell line expressing Cre recombinase, I-Sce I, the adenoviral preterminal protein and polymerase (to increase replication of the HD-vector), i.e., 294G, is used. The helper-virus is based on the two vectors pAdHM4lox and pHM3 lox to generate a first generation virus in which the adenoviral coding sequence is flanked by lox sites. As a marker gene the helper-virus contains the luciferase gene under the control of the SV40 promotor.

Figure 4A:
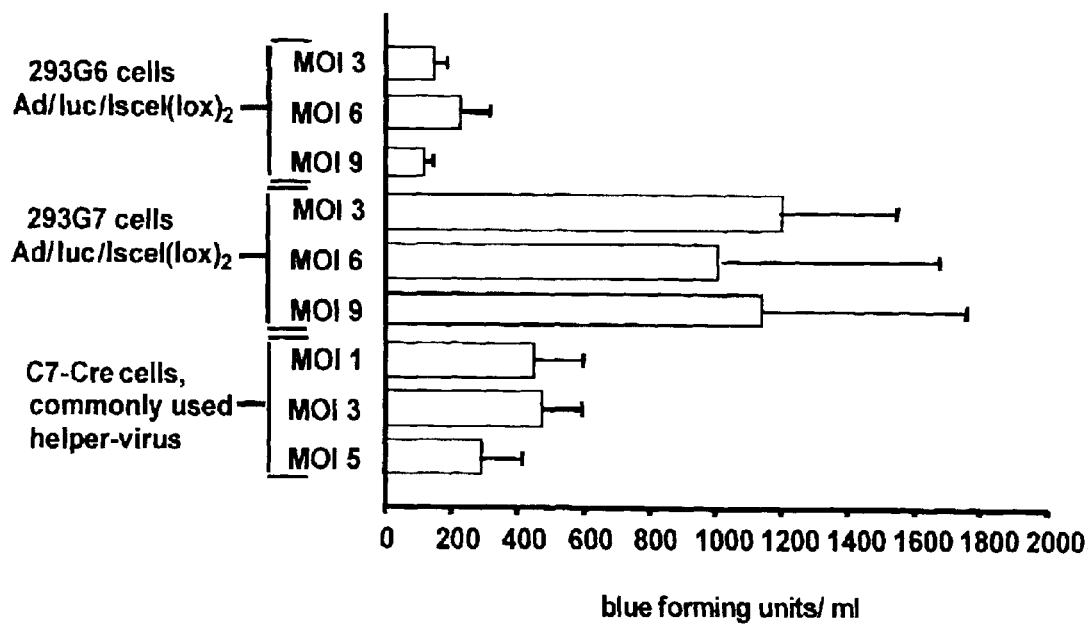
FIGS. 4A and 4B. Comparing Titer and Helper Virus using C7Cre vs. C7Cre/ISceI Cells. AdFTC/lacZ/ChMAR DNA was transfected into two different clonal C7Cre/ISceI cells or our standard C7-Cre cells with varying MOIs of the helper. After the first passage the amount of packaged vector (upper figure) and helper (lower figure) was determined. The vector was titered by dilution and beta-gal analysis on transduced cells while the helper virus was determined by real time PCR.
Figure 4B:
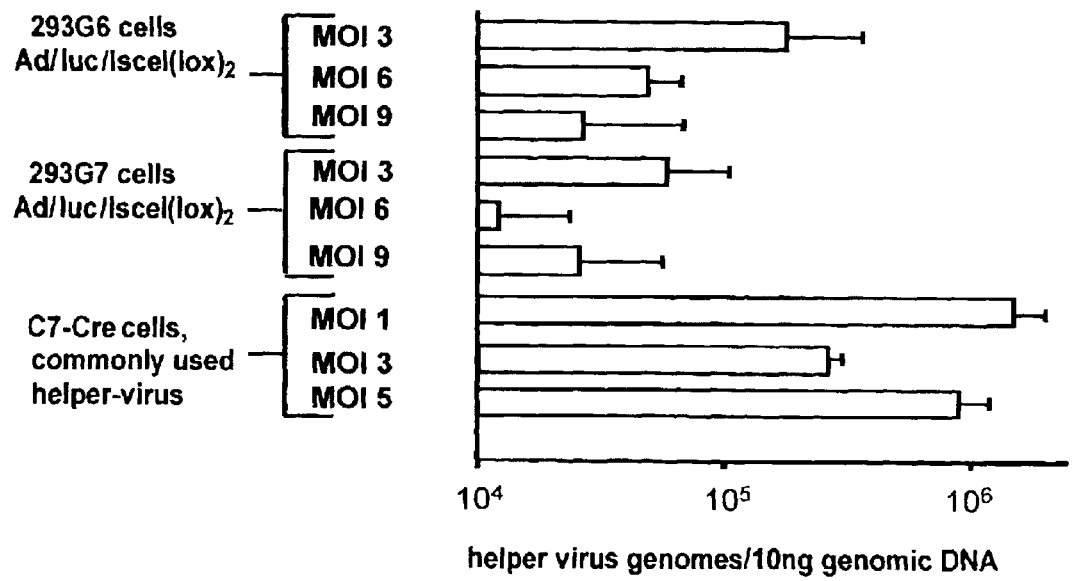

In a preliminary first experiment, high levels of vector and lower levels of helper virus compared to that obtained by our standard methods were obtained after one passage as shown in FIG. 4. In this early preliminary experiment, the greatest vector to helper ratio occurs in the new Cre/SceI cells at an MOI of ~6. Not only is more vector produced using this new cell line but the amount of helper is also greatly reduced.

Figure 5:
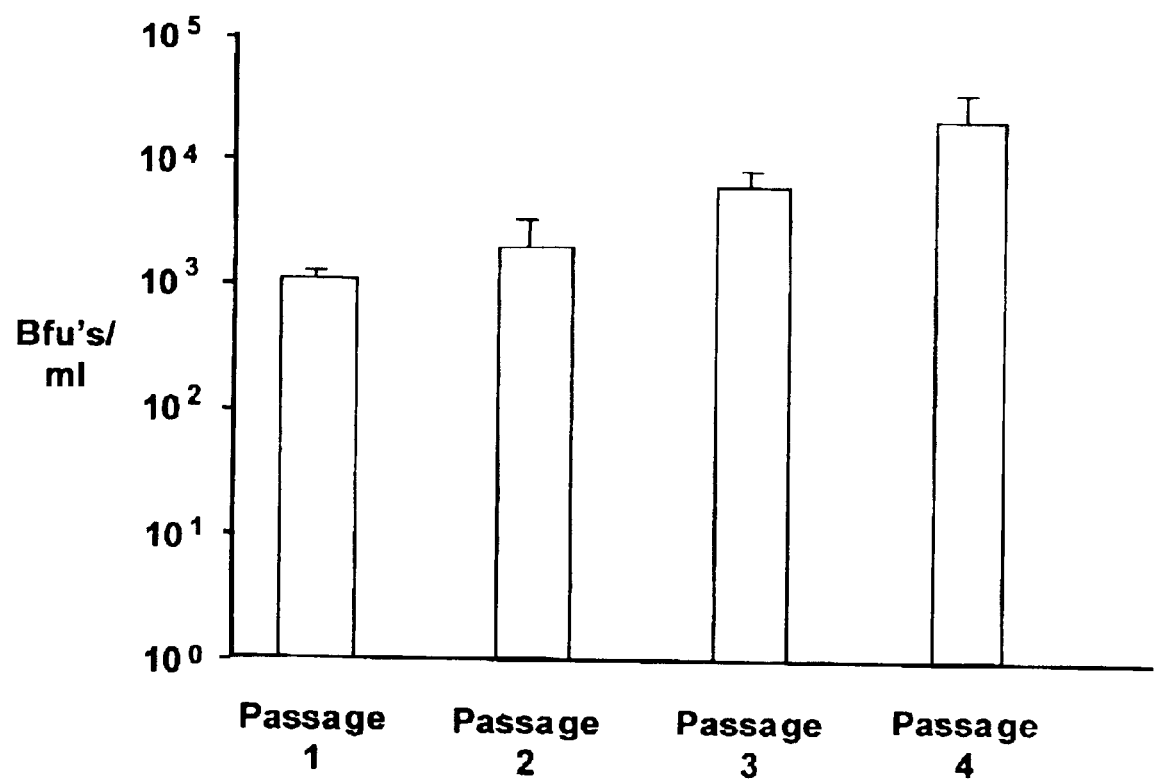
FIG. 5. Serial passaging after transfection of a HD vector that encodes beta-galactosidase. The amplification was done in 293G7 cells end after each round blue forming units (bfu's) per ml were counted.

In a further experiment 4 serial passaging steps were performed to amplify the HD vector AdFTC/lacZ/ChMAR (FIG. 5) using our the cell line 293G7 and the helper virus Adluc/IsceI(lox)$_2$.

III. Preliminary Studies

In a preliminary study, we used the HD vector, AdFTC to express human coagulation factor IX (AdFTC/hFIX). The expression cassette for hFIX contained the enhancers HCR and Apolipoprotein E (ApoE), the human alpha antitrypsin promoter (hAAT), and the hFIX cDNA (includes the hFIX intron A and the bovine polyadenylation signal), which was shown to result in high level gene expression in vivo (Miao et al., 2000, Mol Ther. 1:522–32).

Figure 6A:
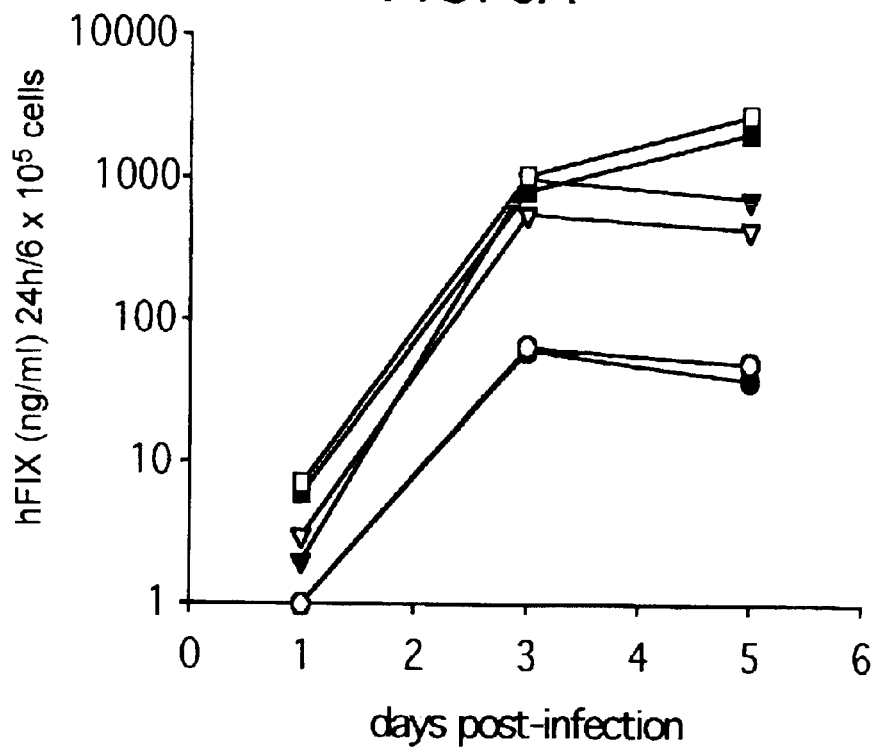
Figure 6B:
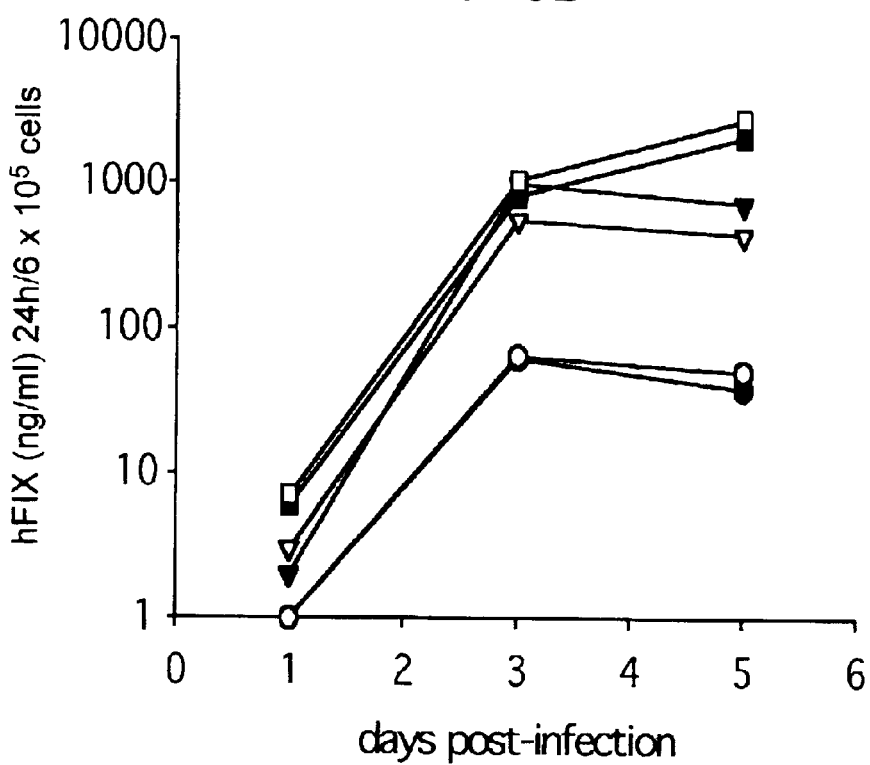

A. Comparison of the Expression Levels in Vitro and in Vivo of a Deleted and a First Generation Adenovirus Containing an Expression Cassette for the Human Coagulation Factor IX In vitro studies in primary hepatocytes demonstrated higher expression levels of hFIX from AdFTC/hFIX compared with a first generation adenovirus (fgAdhFIX) containing the same hFIX expression cassette. FIG. 6 A shows hFIX expression levels for AdFTC/hFIX at different MOIs. For example, at an MOI of 100 for AdFTC/hFIX, hFIX expression levels of up to 2700 ng/ml could be detected. At this MOI the first generation adenovirus with the same expression cassette clearly shows lower expression levels (FIG. 6B). This finding might be due to the cis acting stuffer DNA in the HD vector AdFTC.

Figure 7:
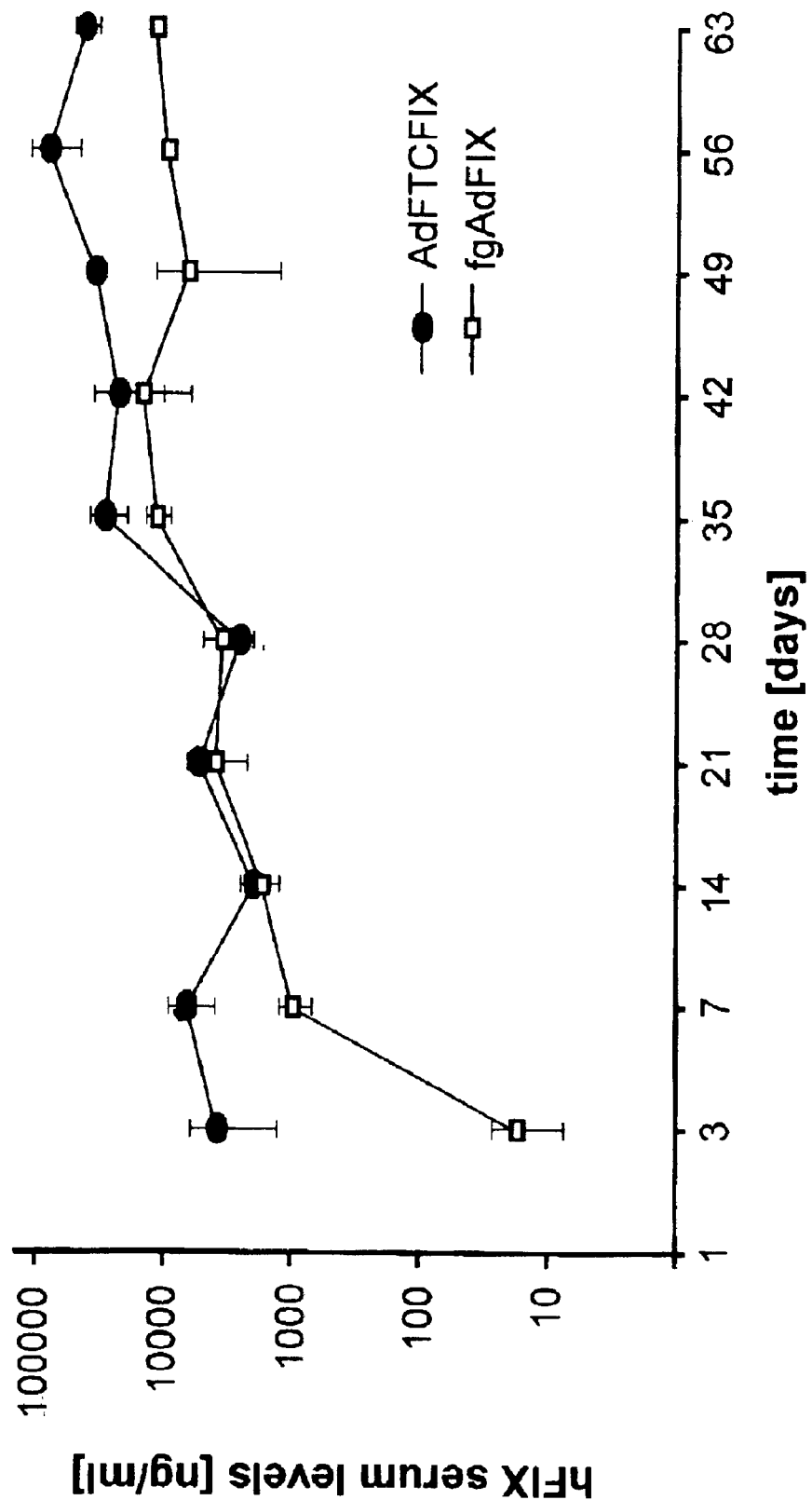
FIG. 7. Transgene expression levels in vivo in C57BL/6 mice for the HD vector AdFTC/hFIX (•) and the first generation adenovirus fgAdhFIX(□). Three individuals per group were injected with 2×10$^9$ infectious particles and hFIX levels were measured by ELISA. +/−SD is shown by error bars.

To study expression levels of AdFTC/hFIX and fgAdhFIX in vivo two groups of three C57BL/6 mice were injected through the tail veins with 2×10$^9$ transducing particles of each virus. Human FIX serum levels were determined every week by ELISA and sustained levels of human FIX could be detected (~41 µg/ml for AdFTC/hFIX and ~11 µg/ml for fgAdFIX 8 weeks after injection). The results are graphically shown in FIG. 7. This observation clearly demonstrates that ADFTC holds great promise as a viral based gene therapy system. No toxicity could be detected in mice injected with AdFTC/hFIX and fgAdhFIX demonstrated by serum alanine aminotransferase (ALT) levels (Table 1).

TABLE 1

Alanine aminotransferase activity (I.U.) in mice receiving adenovirus

| Mouse Group | N | Day 1 [I.U.] | Day 3 [I.U.] | Day 7 [I.U.] | Day 14 [I.U.] | Day 21 [I.U.] |
|---|---|---|---|---|---|---|
| AdFTC/FIX | 3 | 45 +/− 9 | 30 +/− 0.3 | 39 +/− 4.6 | 24 +/− 8.5 | 19 +/− 5.3 |
| FgAdFIX | 3 | 36 +/− 2 | 31 +/− 1.5 | 10 +/− 8.2 | 28 +/− 0.3 | 16 +/− 2.7 |

IV. Strategies for Producing Integrating Gutless Adenovirus

A. Strategy to Produce an Integrating Gutless Adenovirus

Because the persistence of gutted adenoviruses is not known but clearly unlikely to be lifelong, for genetic diseases, a safe integrating adenovirus would have great advantages. Therefore, the second approach proposes the use of our improved less toxic adenoviral system to design adenoviral vectors with the ability to integrate into the genome and therefore, to produce therapeutic genes lifelong. To do this, we transiently express a transposase gene that is non-toxic in liver (Yant et al., 2000 Nature Genetics 25: 35–40) and results in stable integration of DNA seqeunces flanked by a sequence specific (non-mamalian) inverted repeat into chromosomal DNA, with the efficent and clinically relevant delivery properties of the adenovirus capsid. Transposition from a circular genome is much more efficient than from linear DNA. Therefore, we excise the transposon flanked by inverted repeats from the linear adenoviral genome to obtain a circular intermediate with the ability to integrate. Since the Cre-loxP system is already used during production of gutless adenoviruses an alternative system, the Flp recombination system, is used to produce circular intermediate. Therefore, a therapeutic expression cassette flanked by the IRs of transposons is cloned in between Flp recombinase recognition sites (FRT). With transposase and Flp recombinase coexpressed, integration occurs. This approach produces a deleted integrating adenovirus with high integration efficiency. The approach is shown in FIG. 8.

B. Stratagy to Produce a Site Specific Integrating Gutless Adenovirus

A site specific integrase that significantly reduces the potential risk of mutagenesis due to random integration events which occur when AAV or retrovirus is used is provided by using integrases, such as the novel site specific integrases from the Streptomyces phage φC31 (Groth et al., Proc Natl Acad Sci U S A. 200 May 23;97(11):5995–6000.).

V. Placement of an Integrating Transposon into Recombinant Adenoviruses

A.

Figure 9:
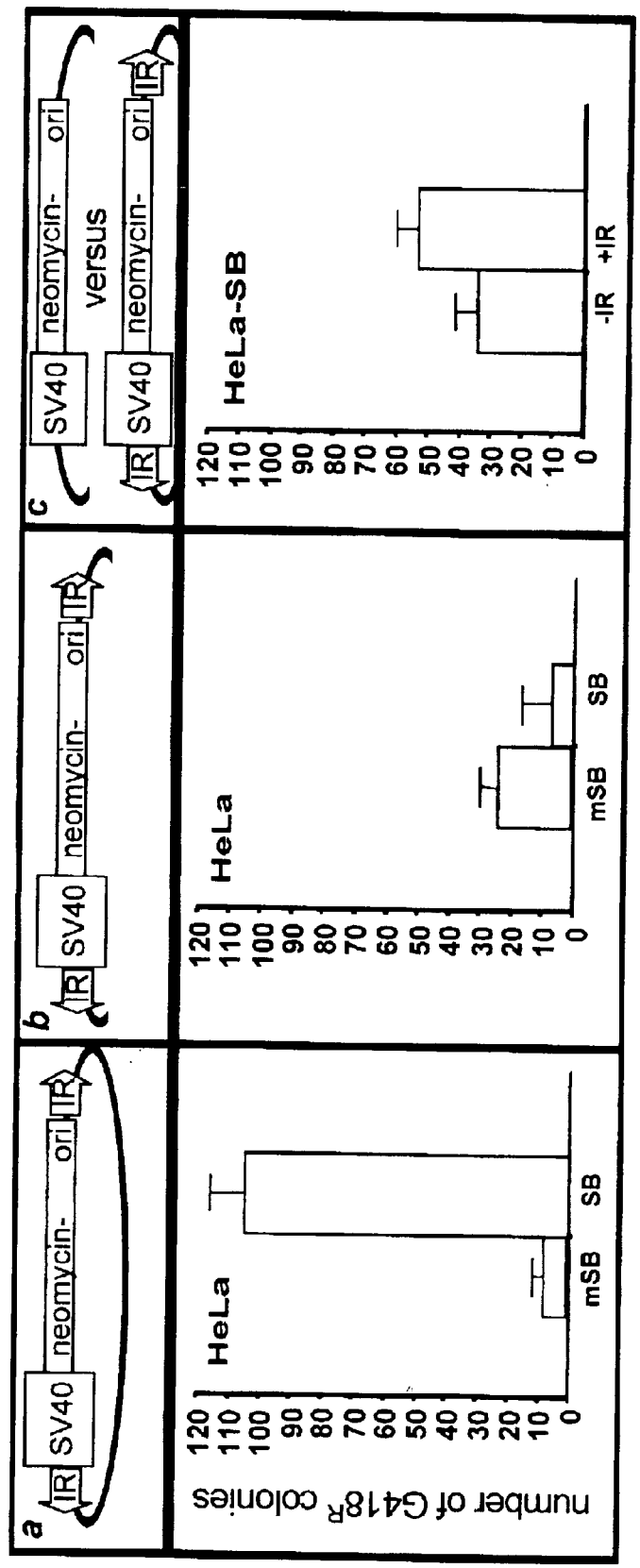
FIG. 9. Transposition does not occur with linear DNA. (a) and (b) Hela cells were transfected with mutant or wildtype transposase and one of the circular or linear plasmids. (c) Transposon IR containing and deficient linear DNAs were transfected into Hela cells that stably express functional transposase. The number of integration events was determined by measuring the number of G418 resistant colonies.
Figure 11A:
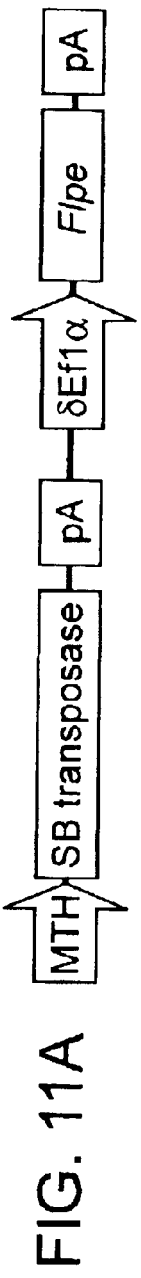
FIGS. 11A, 11B, 11C and 11D. Outlined is the two vector approach to establish a tranposon based integrating gene-deleted vector system. Enh hAAT=enhancer and AAT promoter, MTH=(metal inducible promoter), kan= procaryotic kan resistance gene, ori=bacterial origin of replication, Cm=procaryotic chloramphenical resistance gene. EF1-EF 1 alpha promoter-enhancer.
Figure 11B:
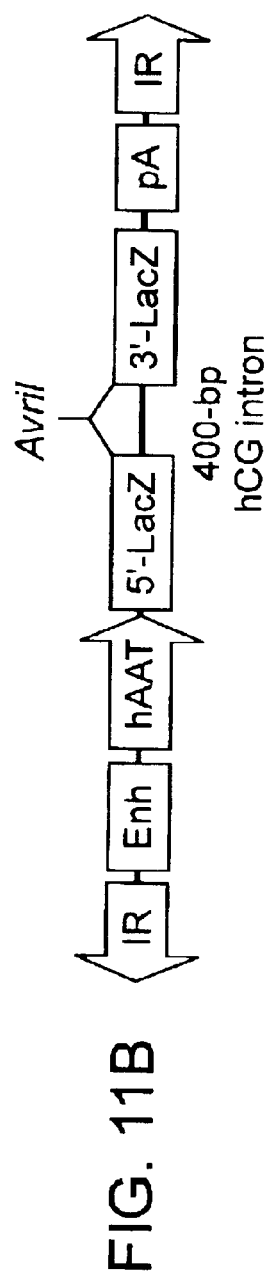
Figure 11C:
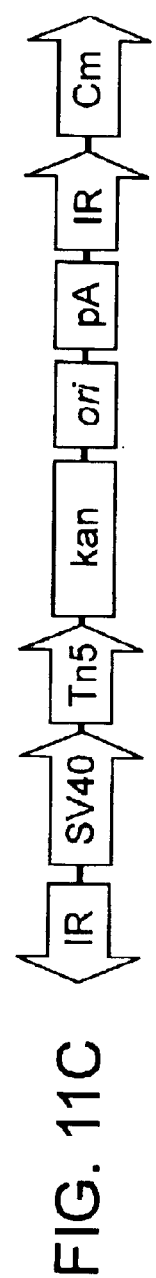
Figure 11D:
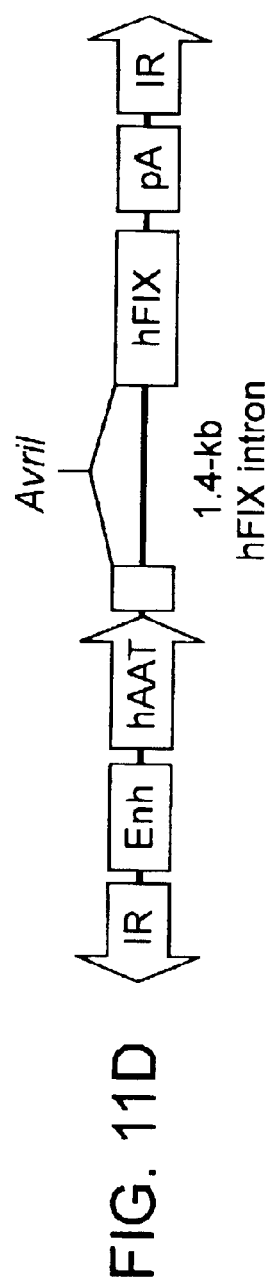

An experiment was performed to determine if the molecular structure (e.g. linear vs circular) of the DNA affects transposition, since the adenovirus vector is a linear DNA molecule. The results of the study were surprising and are summarized in FIG. 9. Various combinations of circular or linear DNA with wildtype or mutant transposases were transfected into HeLa cells. In panel C, there was no increase in stable G418 resistant colonies from linear neomycin phosphotransferase expression cassettes with or without the transposon ITRs in cell lines that constitutively express functional transposase. Thus in order to develop an integrating adenovirus system based on DNA transposition, the molecule will likely have to go through a circular intermediate.

We observed a slow decline in hFIX expression levels. One year post-injection serum hFIX concentrations declined 95% compared to the original levels. Therefore, we proposed a transposon based gene delivery system to produce an adenovirus that was able to integrate an expression cassette into chromosomal DNA. During our studies, we learned that linear DNAs do not efficiently transpose. Thus, we designed a strategy to make the transgene expression cassette circularize allowing it to form a substrate transposase. Our preliminary data shows that the transposon within the adenovirus can indeed circularize when transduced into Hela Cells in vivo. This was demonstrated by transducing cells with the vector described in FIG. 5 followed by Southern blot analysis (FIG. 10).

While a single vector that will also express Flp recombinase (cloned into the region of the stuffer DNA to allow transient expression) is optimal in many embodiments, a two vector system may also be employed. The genomes of the gene-deleted vectors which are being used in a two vector approach are outlined in FIG. 11. The transposase will be driven from an inducible promoter. The expression of Flp recombinase will be from a constitutive and ubiquitous EF1-alpha promoter.

Figure 12:
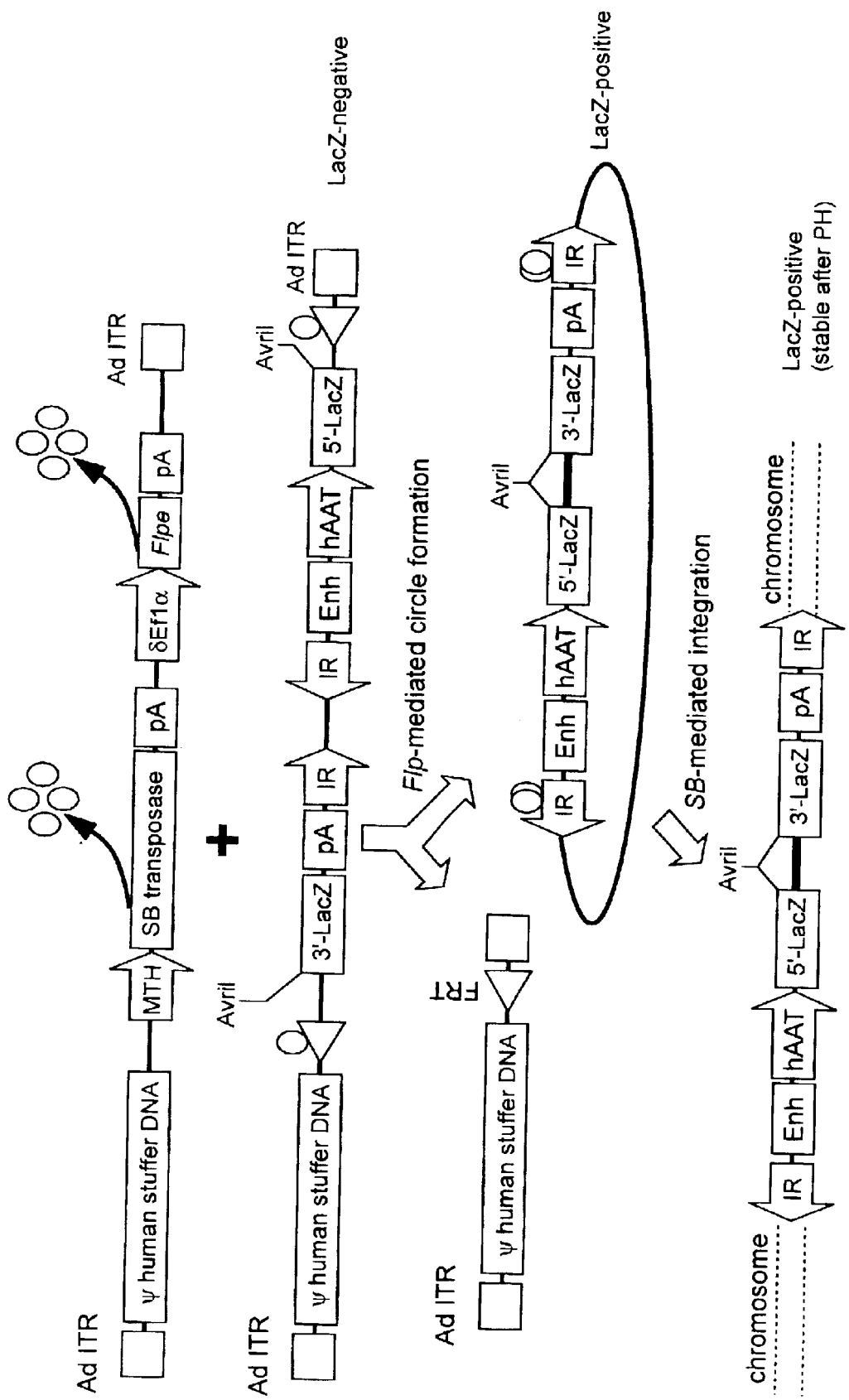
FIG. 12. Method for quantifying integration of adenovirus-transposon vector.

We coadministered the adenoviral vector coexpressing Transposase and Flp recombinase and the vector which contains the kanamycin resistent SB transposon (FIG. 11) into the tail vein of C57B1/6 mice and identified independent transposition events using a recovery strategy which was recently described (Yant et al., Nature Genetics, 2000). The strategy for quantifying integration and therapeutic potential is shown in FIG. 12. Transgene expression cannot occur from the parent adenovirus vector because the expression cassette is split. To establish this, the vector without the FLP/Transposase is injected into mice. However, when the DNA circularizes the intact expression cassette is restored and gene expression can occur. Quantification of gene expression by X-gal staining (frequency of transduced cells), beta-galactosidase enzyme assay or plasma levels of factor IX is performed. The results provide the total amount of gene expression from both circular forms and integrated forms. To establish the amount of gene expression that comes from integrated forms, a ⅔ partial hepatectomy is performed 1 week after vector administration. The removed liver tissue is examined for beta-galactosidase enzyme activity and X-gal staining (in the case of the lac Z vector), and Southern analysis. By using a variety of enzymes that do not cut in the vector, cuts once or twice in the vector, the number of circular genomes is estimated. As the liver regenerates each hepatocyte divides once or twice after partial hepatectomy, and as shown about 95% of non-integrated plasmids are lost. Within two weeks the original liver mass is restored and the amount of gene expression is determined (e.g. beta-galactosidase or plasma factor IX). The advantage of hFIX is that it can be serially determined in individual animals over time. The remaining level of gene expression will result from integrated copies of the transgene. By determining the relative amount of gene expression before and after partial hepatectomy will allow for the relative gene expression from integrated genomes.

B.

1. Introduction

A major limitation of adenovirus-mediated gene therapy for inherited diseases is the instability of transgene expression in vivo, which originates at least in part from the loss of the linear, extrachromosomal vector genomes over time. Herein, we describe the production of a novel low-immunogenic adenovirus gene delivery system that stably maintains virus-encoded transgenes in vivo through integration into host cell chromosomes. This system utilizes a donor transposon vector that, when co-delivered to cells with a helper virus encoding the Flp and Sleeping Beauty (SB) recombinases, undergoes Flp-mediated recombination and excision of its therapeutic payload. This effectively generates transposon circles in situ, which, in marked contrast to linear DNA elements still contained within the adenovirus genome, can readily undergo transposition in the presence of transposase. Systemic in vivo delivery of this system resulted in transposition and stable integration of mouse hepatocytes. Importantly, this level of transposition was sufficient to stabilize in vivo expression of human coagulation factor IX at therapeutic levels (3% of normal) in mice undergoing extensive liver proliferation. Together, these studies demonstrate the feasibility of combining the transduction efficiency and versatility of adenoviral vectors with the integration capabilities of the Sleeping Beauty transposase/transposon system.

2. Integration Efficiency of Linear Nucleic Acids.

Figure 13A:
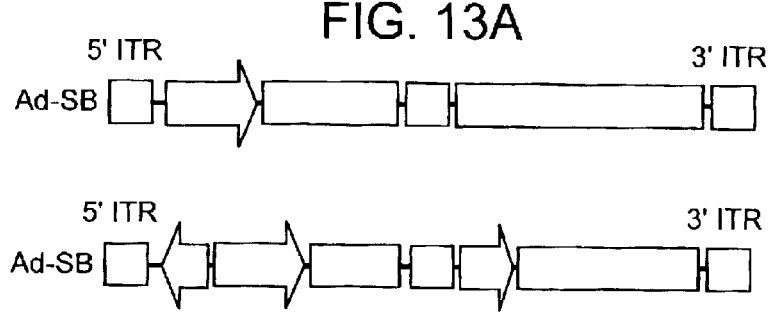
FIGS. 13A, 13B and 13C. Linear DNA genomes do not support transposition.
Figure 13B:
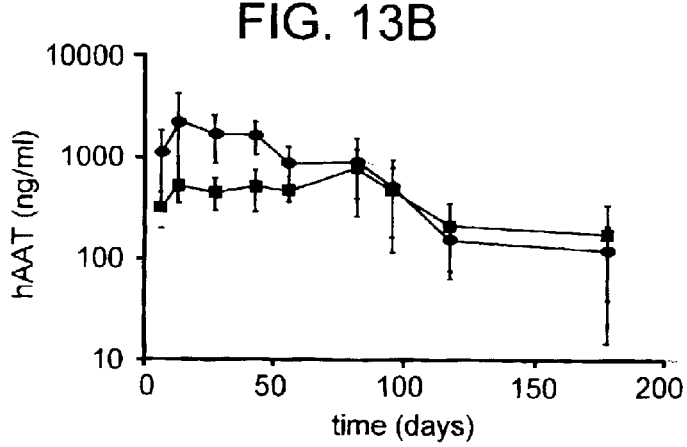
Figure 13C:
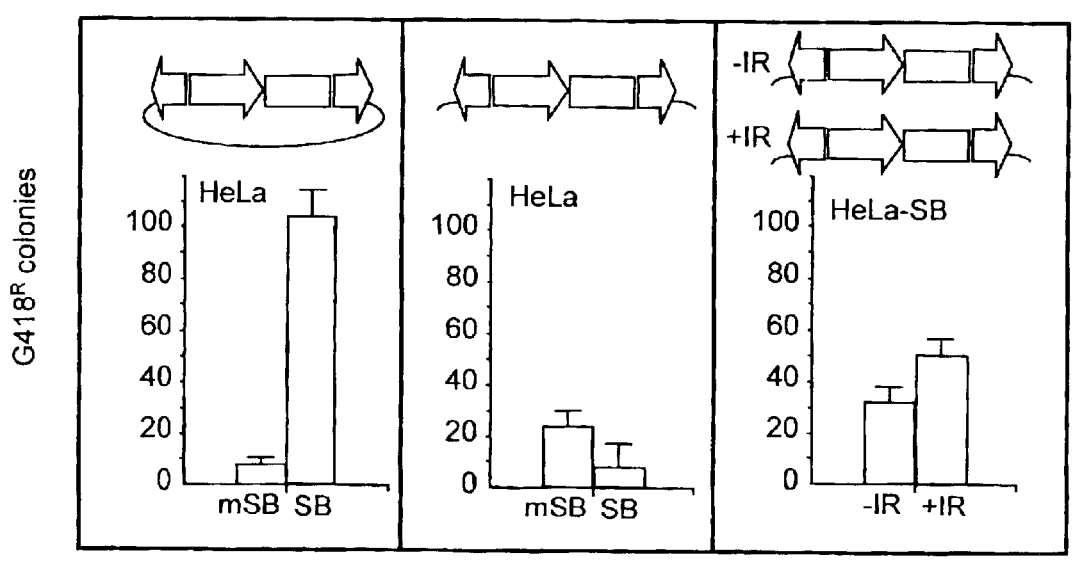

FIG. 13. Linear DNA genomes do not support transposition. A, Structures of the E1/E3-deleted transposition vectors Ad-SB and Ad-ThAAT for in vivo delivery of the Sleeping Beauty transposase/transposon system. 5'ITR and 3' ITR, left and right termini of adenovirus type 5, respectively; RSV, Rous sarcoma virus long terminal repeat promoter; SB, Sleeping Beauty transposase; pA, polyadylation signal; E1/E3; adenovirus type 5 early regions 1 and 3, respectively; IR, Sleeping Beauty inverted repeat sequences; hAAT, human $\alpha_1$-antitrypsin cDNA. B, Long-term adenovirus-based transposon expression in mice in the presence and absence of transposase. C57B1/6 mice (n=5 mice per group) were injected via the tail vein with $2 \times 10^9$ p.f.u. AdThAAT together with $6 \times 10^9$ p.f.u. of either AdSB (•) or Adnull (▼) as a control. C, Transposition efficiency from circular and linear transposable elements in cultured mammalian cells. Left, Transposition of a supercoiled neo-marked transposon in HeLa cells; middle, Transposition frequency of a linearized neo-marked element in HeLa cells; right, Transposition of a linear neo-marked transposon with (−IR) and without (+IR) flanking inverted repeats in HeLa-SB cells, which constitutively express the SB transposase. The mean value±standard deviation of the number of G418-resistant (G418$^R$) colonies obtained after three independent transfections is shown in each panel. SV40, simian virus promoter; neo, neomycin-phosphotransferase gene.

3. Overview of the Strategy to Facilitate Transposition from a Helper-dependent Adenoviral Vector.

Figure 14:
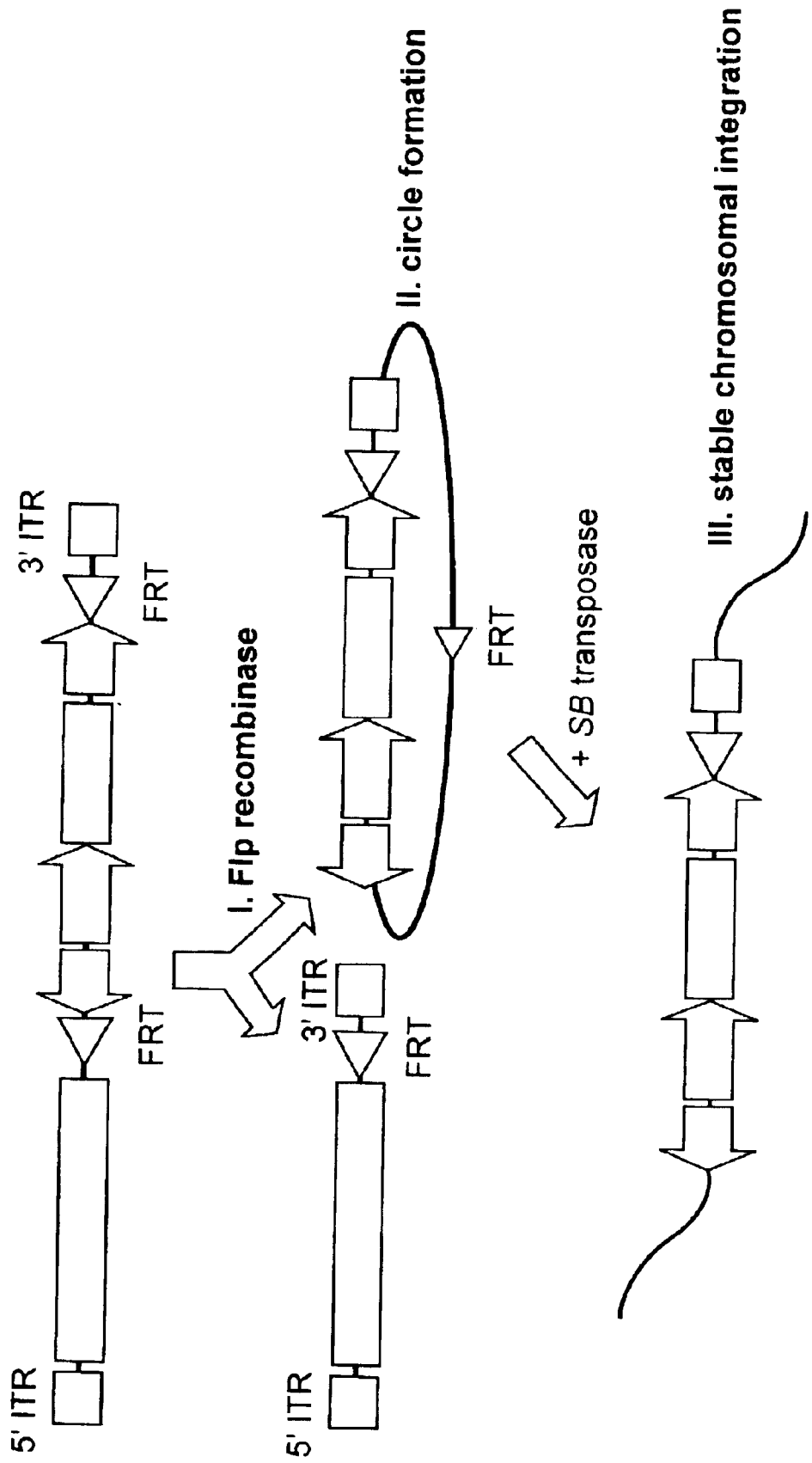
FIG. 14. Overview of the strategy to facilitate transposition from a helper-dependent adenoviral vector.

FIG. 14. An adenoviral vector containing a Sleeping Beauty transposon remains extrachromosomal in SB-expressing cells because the transposase cannot efficiently act upon linear DNA structures. When the transposon is flanked by a pair of Flp recognition target (FRT) sequences, the adenoviral vector undergoes conditional rearrangement in cells co-expressing the Flp recombinase. This rearrangement results in excision of the transposon from the adenovirus genome and its circularization via Flp-mediated recombination. In contrast to their linear counterparts, these circular elements actively undergo DNA-mediated transposition, resulting in stable insertion of the transposon into host cell chromosomes.

4. Structure of Helper-dependent Transposition Vectors.

FIG. 15. We used a two-vector approach to analyze transposition from gutless adenoviral vectors in vivo. This strategy employs the use of one vector to provide the Flp and SB recombinases (A and B) that acts upon a second viral vector containing a donor transposon (C-G). (A) HD-SB-Flp and (B) HD-mSB-Flp both encode the enhanced Flp recombinase (Flpe) necessary for conditional vector rearrangement, but HD-mSB-Flp cannot support transposition due to an inactivating mutation introduced into the transposase gene. The donor vectors (C) HD-FRT-Tnori, (D) HD-Tnori, (E) HD-FRT-TlacZ, (F) HD-TlacZ and (G) HD-FRT-ThFIX contain donor transposons encoding kanamycin (C and D), β-galactosidase (E, F) or human factor IX (G). The intron-containing transgenes in (E-G) are initially split and thus remain inactive until Flp-mediated circularization restores the correct reading frame. The vectors shown in (D) and (F) are control vectors which lack a pair of flanking FRT sites and thus cannot undergo the Flp-mediated recombination necessary for both circle formation and SB-mediated transposition. IgκMAR; two copies of the immunoglobulin κ matrix attachment region; stuffer DNA, a 16.2 kb fragment of alphoid repeat DNA from human chromosome 17; MTH, metallothionein I gene promoter; EF1α, human elongation factor 1α gene enhancer-promoter; Tn5, bacterial promoter; kan, kanamycin resistance gene; ori, p15A bacterial origin of replication; Cm, chloramphenicol resistance gene; LacZ, recombinant split β-galactosidase gene containing intron 1 of the human chorionic gonadotropin (hCG) 6 gene inserted between nucleotides 1,761 and 1,762 of the LacZ coding sequence; ApoE/HCR, 1.2 kb fragment containing the hepatocyte control region (HCR) from the apolipoprotein E (ApoE) gene; hAATp, human $\alpha_1$-antitrypsin gene promoter; hFIX, split human factor IX (hFIX) cDNA containing 1.4 kb truncated intron A from the hFIX gene.

5. Transposition from a Recombinant Helper-dependent Adenoviral Vector Results in the Stable Insertion of Transposon DNA into Mouse Liver Chromosomes in Vivo.

Figure 16A:
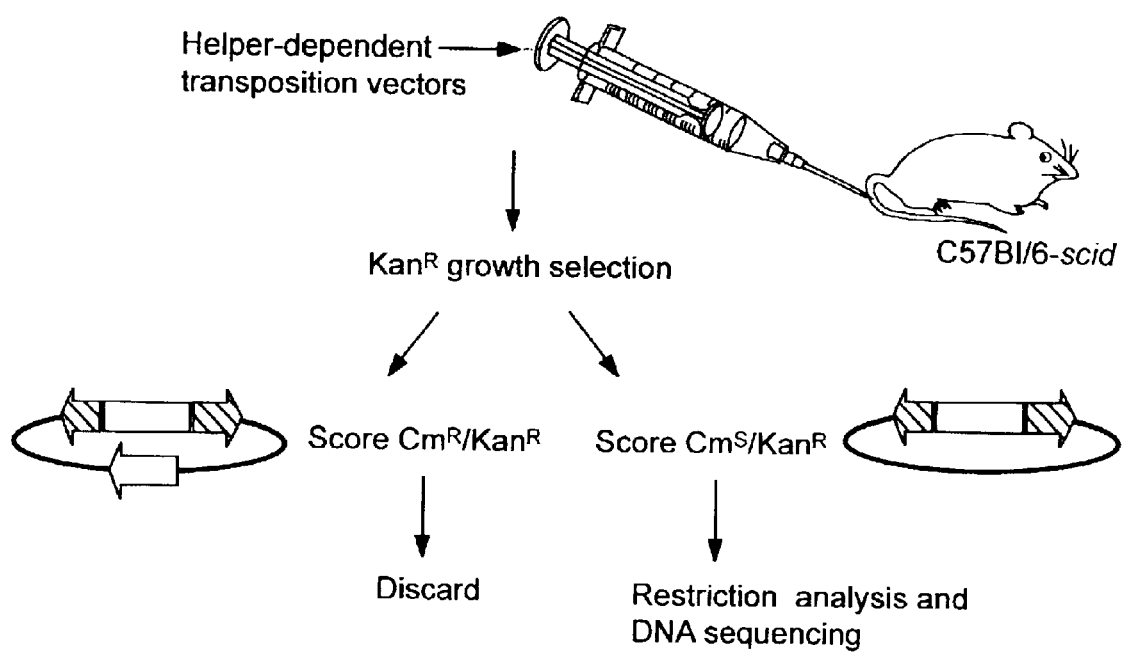

FIG. 16. A, Overview of the genetic approach used to recover transposons from mouse chromosomes. C57B1/6-scid mice (n=2 mice per group) were injected into the tail vein with $1 \times 10_9$ transducing units (T.U.) of each virus. We induced transposase expression in a step-wise manner during the 5 wks immediately following vector administration by addition of increasing concentrations of ZnSO$_4$ to the animal drinking water. Groups 1–3 were included as controls to demonstrate that transposon integration from an adenoviral vector requires both circle formation and transposase activity. B, Structure of the predicted excised circular episome. Numbers represent HindIII fragment sizes in kb and arrows indicate transposase cleavage sites. H, HindIII. C, Transposon DNA analysis by HindIII digestion and ethidium bromide gel electrophoresis. Lanes: 1–8, DNA from eight independent kan$^R$/cam$^S$ clones recovered from the liver DNA of Group 4 (HD-FRT-Tnori+HD-SB-Flp) mice. Arrows indicate internal transposon-specific fragments (2.4 kb and 0.4 kb). Size markers are in kb. D, Transposon insertion site sequences. Target site duplications are shown in bold uppercase, novel flanking sequences are in lowercase and transposon sequences are denoted by the central shaded box. The origin and identity of transposon flanking sequences, shown to the left, were identified through mouse genome database homology searches.

6. In vivo FIX Persistance in Actively Dividing Mouse Livers Via an Adenovirus/transposon System.

Figure 17:
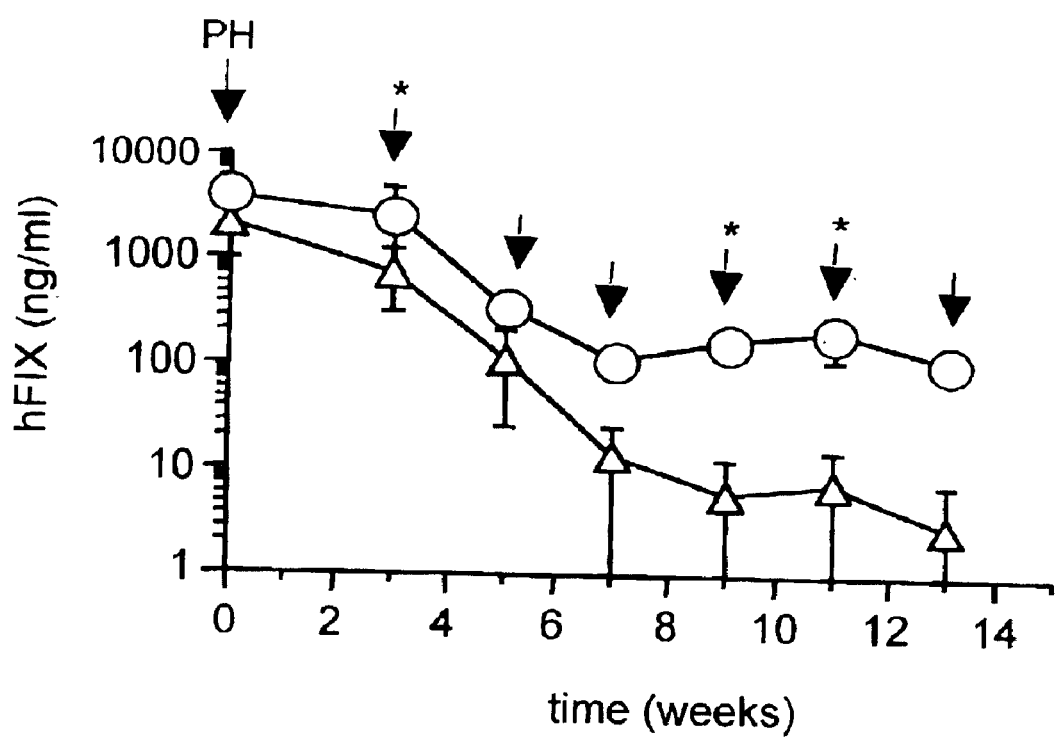
FIG. 17. In vivo FIX persistence in actively dividing mouse livers via an adenovirus/transposon system.
Figure 18A:
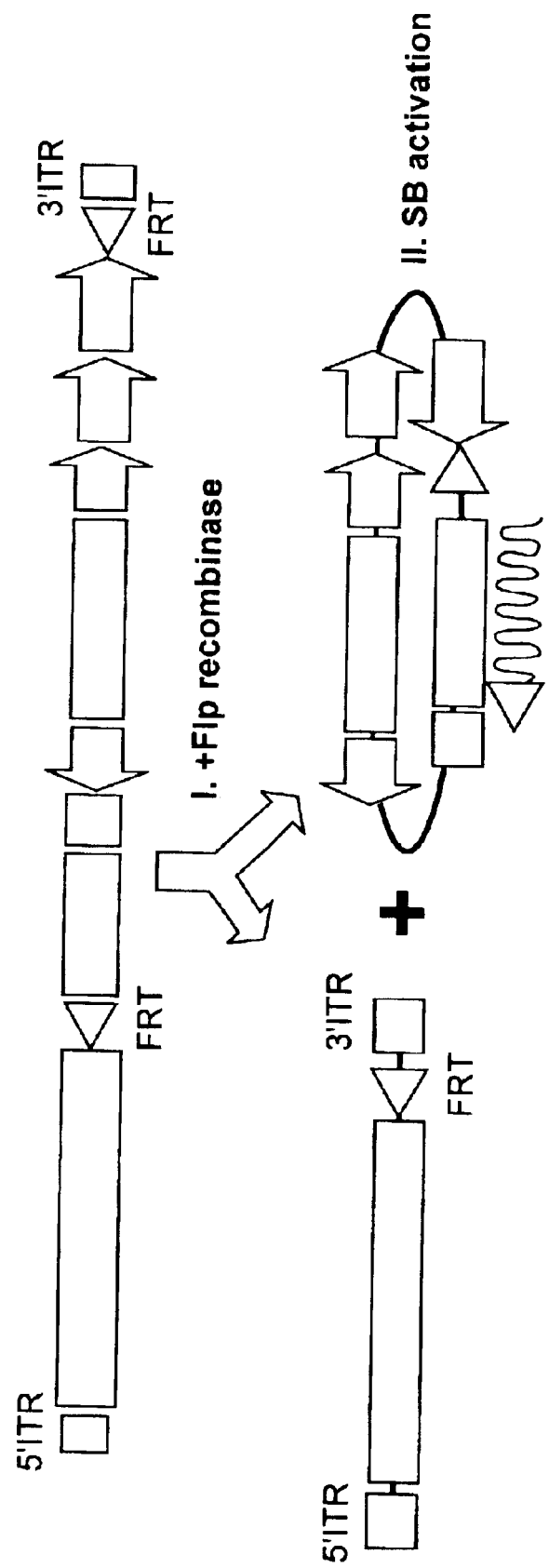

FIG. 17. C57B1/6 mice (n=5 mice per group) were injected into the tail vein with $5 \times 10^8$ T.U. of HD-FRT-ThFIX together with $5 \times 10^8$ of either HD-SB-Flp (●) or HD-mSB-Flp (Δ) as a control. Transposase expression was induced in treated animals during the first 3 wks immediately following vector administration by addition of drinking water containing 25 mM ZnSO$_4$ (final concentration). After three weeks, the Zn was removed from the water and a surgical two/thirds partial hepatectomy (PH) was performed to promoter hepatocellular regeneration and loss of episomal vector. Arrows with astericks (*) illustrate when animals received intraperitoneal (i.p.) injections of carbon tetrachloride (CCl$_4$) at 6, 8, 10, 12 and 14 wks after vector administration to further promote hepatocellular cell-cycling.

VI. Applications for Gene Therapy

In general our new HD dependent vector AdFTC and the two proposed integrating vectors based on AdFTC can be used as an efficient gene-transfer vehicle for gene therapy approaches. For example liver-directed gene transfer to produce therapeutic levels of clotting factors in animal models of haemophilia for phenotypic correction studies can be studied.

VII. Applications for Hepatitis Infections

Gene therapy for hemophilias has been mostly targeted to the liver because it is the natural organ of human FVIII and FIX production but this also presents a problem, since hemophilia is often associated with hepatits infection. One way to address the hepatitis issue in the future is to use this new HD system as a delivery system to the liver for ribozymes which specifically target HCV RNA and cause it to cleave. Based on previous results from this laboratory using a first generation adenovirus which expresses HCV-specific ribozymes the future study of using a HD system to deliver HCV specific ribozymes holds great promise as a way to control HCV replication in the liver.

It is evident from the above results and discussion that the subject invention provides an important new method for making adenoviral vectors. Advantages of the subject invention include the ability to produce high titre preparations of gutless adenoviral vectors with little or no helper vector contamination. In addition, adenoviral vectors are provided in which the exogenous nucleic acid carried by the vector integrates into the target cell genome, which provides for certain advantages in applications where long term expression of the exogenous nucleic acid is desired. As such, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A helper dependent adenoviral vector comprising:
   (a) at least one restriction endonuclease site;
   (b) a stuffer region comprising a nucleic acid having one or more cis-acting sequences found in human genomic nucleic acids; and
   (c) a packaging sequence;
   (d) wherein components (a), (b) and (c) are flanked by adenoviral ITR sequences.

2. An adenoviral helper vector comprising:
   (a) an adenoviral vector coding sequence or portion thereof positioned in a first region between first and second recombinase recognition sites that recombine with each other; and
   (b) at least one endonuclease recognition site not found in mammalian genomic sequences, wherein said endonuclease recognition site is located in a region that is other than said first region.

3. A mammalian cell that stably expresses:
   (a) a recombinase;

(b) an endonuclease that recognizes a sequence not found in mammalian cells;

(c) adenoviral preterminal protein; and (d) adenoviral polymerase.

4. A system for use in producing an adenoviral vector, said system comprising:
 (a) a helper dependent adenoviral vector comprising:
  (i) at least one restriction endonuclease site;
  (ii) a stuffer region made up of a nucleic acid having one or more cis-acting sequences found in human genomic nucleic acids that provide for high level and long-term in vivo expression of a coding sequence present on said vector; and
  (iii) a packaging sequence;
  wherein components (i), (ii) and (iii) are flanked by adenoviral ITR sequences;
 (b) an adenoviral helper vector comprising:
  (i) an adenoviral vector coding sequence or portion thereof positioned in a first region between first and second recombinase recognition sites that recombine with each other and are recognized by a first recombinase; and
  (ii) at least one endonuclease recognition site not found in mammalian genomic sequences, wherein said endonuclease recognition site Is located in a region that is other than said first region; and
 (c) a mammalian cell that stably expresses:
  (i) said first recombinase;
  (ii) an endonuclease that recognizes said endonuclease recognition site not found in mammalian genomic sequences;
  (iii) adenoviral preterminal protein; and
  (iv) adenoviral polymerase.

5. The System according to claim 4, wherein said first recombinase is Crc recombinase and said first and second recombinase recognitions sites are lox sites.

6. The system according to claim 4, wherein said endonuclease expressed in said mammalian cell is I-Sce-I.

7. The system according to claim 4, wherein said mammalian cell is an immortalized human cell.

8. The system according to claim 7, wherein said immortalized human cell is a modified 293 cell.

9. The system according to claim 4, wherein said helper dependent adenoviral vector comprises an expression cassette.

10. The system according to claim 9, wherein said expression cassette is present in an integrating element comprising said expression cassette flanked by sites recognized by a DNA insertion mediating enzyme.

11. The system according to claim 10, wherein said DNA insertion mediating enzyme is a transposase and said integrating element is a transposon.

12. The system according to claim 11, wherein said DNA insertion mediating enzyme is an integrase.

13. The system according to claim 10, wherein said integrating element is flanked by third and fourth recombinase recognition sites that recombine with each other and are recognized by a second recombinase but not said first recombinase.

14. A kit for use in preparing virions made up of a helper dependent adenoviral vector encapsulated in an adenoviral capsid protein, said kit comprising:
 (a) a helper dependent adenoviral vector comprising:
  (i) at least one restriction endonuclease site;
  (ii) a stuffer region made up of a nucleic acid having one or more cis-acting sequences found in human genomic nucleic acids that provide for high level and long-term in vivo expression of a coding sequence present on said vector; and
  (iii) a packaging sequence;
  wherein components (i), (ii) and (iii) are flanked by adenoviral ITR sequences;
 (b) an adenoviral helper vector comprising:
  (i) an adenoviral vector coding sequence or portion thereof positioned in a first region between first and second recombinase recognition sites that recombine with each other; and
  (ii) at least one endonuclease recognition site not found in mammalian genomic sequences, wherein said endonuclease recognition site is located in a region that is other than said first region; and
 (c) a mammalian cell that stably expresses:
  (i) a recombinase that recognizes said first and second recombinase recognition sites of said adenoviral helper vector;
  (ii) an endonuclease that recognizes said endonuclease recognition site not found in mammalian genomic sequences;
  (iii) adenoviral preterminal protein; and
  (iv) adenoviral polymerase.

15. An adenoviral vector comprising:
 an integrating element, and
 a nucleic acid sequence having one or more cis-acting sequences found in human genomic nucleic acids.

16. The adenoviral vector according to claim 15, wherein said integrating element is an expression cassette.

17. A method of introducing a nucleic acid into target cell, said method comprising:
 contacting said target cell with an adenoviral vector according to claim 15 to introduce a nucleic acid into said target cell.

18. The method according to claim 17, wherein said nucleic acid is an expression cassette.

19. The method according to claim 17, wherein said method is a method of integrating said nucleic acid into a chromosome of said target cell.

20. The system according to claim 7, wherein said immortalized human cell is a 294G cell.

21. A method of introducing a nucleic acid into a target cell, said method comprising:
 contacting said target cell with an adenoviral vector according to claim 1 to introduce a nucleic acid into said target cell, wherein said adenoviral vector further includes an integrating element.

22. The method according to claim 21, wherein said nucleic acid is an expression cassette.

23. The method according to claim 21, wherein said method is a method of integrating said nucleic acid into a chromosome of said target cell.

24. The helper dependent adenoviral vector according to claim 1, wherein said stuffer region is made up of a nucleic acid having one or more cu-acting sequences found in human genomic nucleic acids that provide for high level and long-term in vivo expression of a coding sequence present on said vector.

25. The helper dependent adenoviral vector according to claim 1, wherein said at least one restriction endonuclease site is part of a multiple cloning site made up of a plurality of distinct restriction endonuclease sites.

26. The helper dependent adenoviral vector according to claim 1, wherein said vector further comprises an expression cassette.

27. The helper dependent adenoviral vector according to claim 26, wherein said expression cassette is present in an integrating element comprising said expression cassette flanked by sites recognized by a DNA insertion mediating enzyme.

28. The helper dependent adenoviral vector according to claim 27, wherein said DNA insertion mediating enzyme is a transposase and said integrating element is a transposon.

29. The helper dependent adenoviral vector according to claim 27, wherein said DNA insertion mediating enzyme is an integrase.

30. The helper dependent adenoviral vector according to claim 27, wherein said vector further comprises according sequence for said DNA insertion mediating enzyme.

31. The helper dependent adenoviral vector according to claim 27, wherein said integrating element is flanked by recombinase recognition sites that recombinase with each other.

32. The helper dependent adenoviral vector according to claim 1, wherein said vector is a linear nucleic acid.

33. The helper dependent adenoviral vector according to claim 1, wherein said vector is present in a virion that comprises an adenoviral capsid.

34. The helper dependent adenoviral vector according to claim 1, wherein said vector is a circular nucleic acid.

35. The adenoviral helper vector according to claim 2, wherein said first and second recombinase recognition sites are lox sites.

36. The adenoviral helper vector according to claim 2, wherein said endonuclease recognition site is a non-palindromic stretch of nucleotides ranging in length from about 15 to 25 nt.

37. The adenoviral helper vector according to claim 36, wherein said endonuclease recognition site is the 18 bp 1-Sce I site.

38. The adenoviral helper vector according to claim 2, wherein said vector is linear.

39. The adenoviral helper vector according to claim 38, wherein said vector is present in a virion that comprises an adenoviral capsid.

40. The adenoviral helper vector according to claim 2, wherein said vector is circular.

41. The kit according to claim 14, wherein said recombinase is Cre recombinase and said first and second recombinase recognitions sites are lox sites.

42. The kit according to claim 14, wherein said endonuclease is I-See-I.

43. The kit according to claim 14, wherein said mammalian cell is an immortalized human cell.

44. The kit according to claim 43, wherein said immortalized human cell is a 293 cell.

45. The kit according to claim 43, wherein said immortalized human cell is a 294G cell.

* * * * *

UNITED STATES PATENT AND TRADEMARK OFFICE
CERTIFICATE OF CORRECTION

PATENT NO. : 6,943,012 B2
DATED : September 13, 2005
INVENTOR(S) : Ehrhardt Anja et al.

It is certified that error appears in the above-identified patent and that said Letters Patent is hereby corrected as shown below:

Column 33,
Line 25, change "Is" to -- is --;
Line 35, change "Crc" to -- Cre --;

Column 34,
Line 57, change "cu-acting" to -- cis-acting --;
Line 64, change "distinet" to -- distinct --;

Column 35,
Line 13, change "according" to -- a coding --; and
Line 17, change "recombinase" to -- recombine --.

Signed and Sealed this

Fifteenth Day of November, 2005

JON W. DUDAS
*Director of the United States Patent and Trademark Office*

SEQUENCE LISTING

```
<160> NUMBER OF SEQ ID NOS: 36

<210> SEQ ID NO 1
<211> LENGTH: 16
<212> TYPE: DNA
<213> ORGANISM: Artificial Sequence
<220> FEATURE:
<223> OTHER INFORMATION: oligonucleotide

<400> SEQUENCE: 1
aggaaatagg acatta                                                    16

<210> SEQ ID NO 2
<211> LENGTH: 16
<212> TYPE: DNA
<213> ORGANISM: Artificial Sequence
<220> FEATURE:
<223> OTHER INFORMATION: oligonucleotide

<400> SEQUENCE: 2
taggtgaggc aggaca                                                    16

<210> SEQ ID NO 3
<211> LENGTH: 17
<212> TYPE: DNA
<213> ORGANISM: Artificial Sequence
<220> FEATURE:
<223> OTHER INFORMATION: oligonucleotide

<400> SEQUENCE: 3
gtttcagagc atgtgta                                                   17

<210> SEQ ID NO 4
<211> LENGTH: 17
<212> TYPE: DNA
<213> ORGANISM: Artificial Sequence
<220> FEATURE:
<223> OTHER INFORMATION: oligonucleotide

<400> SEQUENCE: 4
tagctcttgc agaggac                                                   17

<210> SEQ ID NO 5
<211> LENGTH: 17
```

```
<212> TYPE: DNA
<213> ORGANISM: Artificial Sequence
<220> FEATURE:
<223> OTHER INFORMATION: oligonucleotide

<400> SEQUENCE: 5
actacattgt ggaaata                                                  17

<210> SEQ ID NO 6
<211> LENGTH: 17
<212> TYPE: DNA
<213> ORGANISM: Artificial Sequence
<220> FEATURE:
<223> OTHER INFORMATION: oligonucleotide

<400> SEQUENCE: 6
tataccacat tttctgt                                                  17

<210> SEQ ID NO 7
<211> LENGTH: 17
<212> TYPE: DNA
<213> ORGANISM: Artificial Sequence
<220> FEATURE:
<223> OTHER INFORMATION: oligonucleotide

<400> SEQUENCE: 7
ttagtgggaa gtatata                                                  17

<210> SEQ ID NO 8
<211> LENGTH: 17
<212> TYPE: DNA
<213> ORGANISM: Artificial Sequence
<220> FEATURE:
<223> OTHER INFORMATION: oligonucleotide

<400> SEQUENCE: 8
tatgcccatg tgaaagc                                                  17

<210> SEQ ID NO 9
<211> LENGTH: 17
<212> TYPE: DNA
<213> ORGANISM: Artificial Sequence
<220> FEATURE:
<223> OTHER INFORMATION: oligonucleotide

<400> SEQUENCE: 9
caaagagaaa gcaggta                                                  17

<210> SEQ ID NO 10
<211> LENGTH: 17
<212> TYPE: DNA
<213> ORGANISM: Artificial Sequence
<220> FEATURE:
<223> OTHER INFORMATION: oligonucleotide

<400> SEQUENCE: 10
tagcttgcag tgggctt                                                  17

<210> SEQ ID NO 11
<211> LENGTH: 18
<212> TYPE: DNA
<213> ORGANISM: Artificial Sequence
<220> FEATURE:
<223> OTHER INFORMATION: oligonucleotide

<400> SEQUENCE: 11
```

```
agaacacatc cctacgta                                                 18

<210> SEQ ID NO 12
<211> LENGTH: 17
<212> TYPE: DNA
<213> ORGANISM: Artificial Sequence
<220> FEATURE:
<223> OTHER INFORMATION: oligonucleotide

<400> SEQUENCE: 12
tataggcaat agctgtt                                                  17

<210> SEQ ID NO 13
<211> LENGTH: 17
<212> TYPE: DNA
<213> ORGANISM: Artificial Sequence
<220> FEATURE:
<223> OTHER INFORMATION: oligonucleotide

<400> SEQUENCE: 13
tgagtcaatc agaccta                                                  17

<210> SEQ ID NO 14
<211> LENGTH: 17
<212> TYPE: DNA
<213> ORGANISM: Artificial Sequence
<220> FEATURE:
<223> OTHER INFORMATION: oligonucleotide

<400> SEQUENCE: 14
taaatccaag gtcagcc                                                  17

<210> SEQ ID NO 15
<211> LENGTH: 17
<212> TYPE: DNA
<213> ORGANISM: Artificial Sequence
<220> FEATURE:
<223> OTHER INFORMATION: oligonucleotide

<400> SEQUENCE: 15
aagttcattt caaaata                                                  17

<210> SEQ ID NO 16
<211> LENGTH: 17
<212> TYPE: DNA
<213> ORGANISM: Artificial Sequence
<220> FEATURE:
<223> OTHER INFORMATION: oligonucleotide

<400> SEQUENCE: 16
tagtacttga tcacctt                                                  17

<210> SEQ ID NO 17
<211> LENGTH: 17
<212> TYPE: DNA
<213> ORGANISM: Artificial Sequence
<220> FEATURE:
<223> OTHER INFORMATION: oligonucleotide

<400> SEQUENCE: 17
agagagacaa agaagta                                                  17

<210> SEQ ID NO 18
<211> LENGTH: 17
<212> TYPE: DNA
<213> ORGANISM: Artificial Sequence
```

```
<220> FEATURE:
<223> OTHER INFORMATION: oligonucleotide

<400> SEQUENCE: 18
tatgatatga aaacctg                                                  17

<210> SEQ ID NO 19
<211> LENGTH: 17
<212> TYPE: DNA
<213> ORGANISM: Artificial Sequence
<220> FEATURE:
<223> OTHER INFORMATION: oligonucleotide

<400> SEQUENCE: 19
aaacacaaaa gctaata                                                  17

<210> SEQ ID NO 20
<211> LENGTH: 17
<212> TYPE: DNA
<213> ORGANISM: Artificial Sequence
<220> FEATURE:
<223> OTHER INFORMATION: oligonucleotide

<400> SEQUENCE: 20
taaatatgtt ttcaaaa                                                  17

<210> SEQ ID NO 21
<211> LENGTH: 17
<212> TYPE: DNA
<213> ORGANISM: Artificial Sequence
<220> FEATURE:
<223> OTHER INFORMATION: oligonucleotide

<400> SEQUENCE: 21
ctactgtcta gctttta                                                  17

<210> SEQ ID NO 22
<211> LENGTH: 17
<212> TYPE: DNA
<213> ORGANISM: Artificial Sequence
<220> FEATURE:
<223> OTHER INFORMATION: oligonucleotide

<400> SEQUENCE: 22
tatatgaagc tatttcc                                                  17

<210> SEQ ID NO 23
<211> LENGTH: 17
<212> TYPE: DNA
<213> ORGANISM: Artificial Sequence
<220> FEATURE:
<223> OTHER INFORMATION: oligonucleotide

<400> SEQUENCE: 23
tttttcactg cattcta                                                  17

<210> SEQ ID NO 24
<211> LENGTH: 17
<212> TYPE: DNA
<213> ORGANISM: Artificial Sequence
<220> FEATURE:
<223> OTHER INFORMATION: oligonucleotide

<400> SEQUENCE: 24
tagttgtggt ttgtcca                                                  17
```

```
<210> SEQ ID NO 25
<211> LENGTH: 17
<212> TYPE: DNA
<213> ORGANISM: Artificial Sequence
<220> FEATURE:
<223> OTHER INFORMATION: oligonucleotide

<400> SEQUENCE: 25
tagagtttct aaatata                                                    17

<210> SEQ ID NO 26
<211> LENGTH: 17
<212> TYPE: DNA
<213> ORGANISM: Artificial Sequence
<220> FEATURE:
<223> OTHER INFORMATION: oligonucleotide

<400> SEQUENCE: 26
tataactaag aaattaa                                                    17

<210> SEQ ID NO 27
<211> LENGTH: 17
<212> TYPE: DNA
<213> ORGANISM: Artificial Sequence
<220> FEATURE:
<223> OTHER INFORMATION: oligonucleotide

<400> SEQUENCE: 27
acccagcttg tgagtta                                                    17

<210> SEQ ID NO 28
<211> LENGTH: 17
<212> TYPE: DNA
<213> ORGANISM: Artificial Sequence
<220> FEATURE:
<223> OTHER INFORMATION: oligonucleotide

<400> SEQUENCE: 28
tacatcagtt gacaccc                                                    17

<210> SEQ ID NO 29
<211> LENGTH: 17
<212> TYPE: DNA
<213> ORGANISM: Artificial Sequence
<220> FEATURE:
<223> OTHER INFORMATION: oligonucleotide

<400> SEQUENCE: 29
ggctgagatc aaaggta                                                    17

<210> SEQ ID NO 30
<211> LENGTH: 17
<212> TYPE: DNA
<213> ORGANISM: Artificial Sequence
<220> FEATURE:
<223> OTHER INFORMATION: oligonucleotide

<400> SEQUENCE: 30
tagatcacgc caggtag                                                    17

<210> SEQ ID NO 31
<211> LENGTH: 17
<212> TYPE: DNA
<213> ORGANISM: Artificial Sequence
<220> FEATURE:
<223> OTHER INFORMATION: oligonucleotide
```

<400> SEQUENCE: 31
tgagtcaatc agaccta 17

<210> SEQ ID NO 32
<211> LENGTH: 17
<212> TYPE: DNA
<213> ORGANISM: Artificial Sequence
<220> FEATURE:
<223> OTHER INFORMATION: oligonucleotide

<400> SEQUENCE: 32
taaatccaag gtcagcc 17

<210> SEQ ID NO 33
<211> LENGTH: 17
<212> TYPE: DNA
<213> ORGANISM: Artificial Sequence
<220> FEATURE:
<223> OTHER INFORMATION: oligonucleotide

<400> SEQUENCE: 33
tgaggtctta ggattta 17

<210> SEQ ID NO 34
<211> LENGTH: 17
<212> TYPE: DNA
<213> ORGANISM: Artificial Sequence
<220> FEATURE:
<223> OTHER INFORMATION: oligonucleotide

<400> SEQUENCE: 34
tacaaggaaa gatatga 17

<210> SEQ ID NO 35
<211> LENGTH: 17
<212> TYPE: DNA
<213> ORGANISM: Artificial Sequence
<220> FEATURE:
<223> OTHER INFORMATION: oligonucleotide

<400> SEQUENCE: 35
acttattgta cattata 17

<210> SEQ ID NO 36
<211> LENGTH: 17
<212> TYPE: DNA
<213> ORGANISM: Artificial Sequence
<220> FEATURE:
<223> OTHER INFORMATION: oligonucleotide

<400> SEQUENCE: 36
taatatcaat taattca 17